US008080257B2

(12) United States Patent
Kanji et al.

(10) Patent No.: US 8,080,257 B2
(45) Date of Patent: *Dec. 20, 2011

(54) COSMETIC COMPOSITIONS CONTAINING AT LEAST ONE HETERO POLYMER AND AT LEAST ONE FILM-FORMING SILICONE RESIN AND METHODS OF USING

(75) Inventors: Mohamed Kanji, Edison, NJ (US); Carl Orr, Scotch Plains, NJ (US); Carlos O. Pinzon, New Milford, NJ (US)

(73) Assignee: L'Oreal S.A. (FR)

( * ) Notice: Subject to any disclaimer, the term of this patent is extended or adjusted under 35 U.S.C. 154(b) by 436 days.

This patent is subject to a terminal disclaimer.

(21) Appl. No.: 09/733,899

(22) Filed: Dec. 12, 2000

(65) Prior Publication Data
US 2002/0114773 A1    Aug. 22, 2002

(51) Int. Cl.
A61Q 1/00        (2006.01)
A61Q 1/10        (2006.01)
(52) U.S. Cl. ...................... 424/401; 424/70.7
(58) Field of Classification Search ............... 424/400, 424/401, 65, 63, 64, 59, 70.1, 70.6, 70.7, 424/70.9, 70.11, 70.12, 70.121, 70.122, 70.17, 424/61, 62
See application file for complete search history.

(56) References Cited

U.S. PATENT DOCUMENTS

| | | |
|---|---|---|
| 2,379,413 A | 7/1945 | Bradley |
| 2,450,940 A | 10/1948 | Cowan et al. |
| 2,463,264 A | 3/1949 | Graenacher |
| 2,662,068 A | 12/1953 | Floyd |
| 2,663,649 A | 12/1953 | Winkler |
| 2,890,097 A | 6/1959 | Coe |
| 2,962,461 A | 11/1960 | Toussaint et al. |
| 3,086,914 A | 4/1963 | Soloway |
| 3,141,787 A | 7/1964 | Goetze et al. |
| 3,148,125 A | 9/1964 | Strianse et al. |
| 3,156,572 A | 11/1964 | Carlick et al. |
| 3,157,681 A | 11/1964 | Fischer |
| 3,255,082 A | 6/1966 | Barton |
| 3,324,041 A | 6/1967 | Sommer et al. |
| 3,341,465 A | 9/1967 | Kaufman et al. |
| 3,412,115 A | 11/1968 | Floyd et al. |
| 3,615,289 A | 10/1971 | Felton |
| 3,645,705 A | 2/1972 | Miller et al. |
| 3,778,394 A | 12/1973 | Lovald et al. |
| 3,819,342 A | 6/1974 | Gunderman et al. |
| 3,857,960 A | 12/1974 | Mackles |
| 3,926,655 A | 12/1975 | Miles |
| 3,937,811 A | 2/1976 | Papantoniou et al. |
| 3,969,087 A | 7/1976 | Saito et al. |
| 4,049,792 A | 9/1977 | Elsnau |
| 4,051,159 A | 9/1977 | Tsoucalas et al. |
| 4,062,819 A | 12/1977 | Mains et al. |
| RE29,871 E | 12/1978 | Papantoniou et al. |
| 4,128,436 A | 12/1978 | O'Hara et al. |
| 4,137,306 A | 1/1979 | Rubino et al. |
| 4,148,875 A | 4/1979 | Barnett et al. |
| 4,150,002 A | 4/1979 | Drawert et al. |
| 4,247,411 A | 1/1981 | Vanlerberghe et al. |
| 4,275,054 A | 6/1981 | Sebag et al. |
| 4,275,055 A | 6/1981 | Nachtigal et al. ............... 424/70 |
| 4,279,658 A | 7/1981 | Harvey et al. |
| 4,337,298 A | 6/1982 | Karim et al. |
| 4,341,671 A | 7/1982 | Bolze et al. |
| 4,376,194 A | 3/1983 | Tanaka et al. |
| 4,387,090 A | 6/1983 | Bolich, Jr. |
| 4,438,240 A | 3/1984 | Tanaka et al. |
| 4,466,936 A | 8/1984 | Schapel |
| 4,536,405 A | 8/1985 | Nara et al. |
| 4,552,693 A | 11/1985 | Hussain et al. |
| 4,571,267 A | 2/1986 | Drawert et al. |
| 4,620,492 A | 11/1986 | Vogg et al. |
| 4,655,836 A | 4/1987 | Drawert et al. |
| 4,663,428 A | 5/1987 | Okitu et al. |
| 4,699,779 A | 10/1987 | Palinczar |
| 4,699,924 A | 10/1987 | Durrant et al. |
| 4,712,571 A | 12/1987 | Remz et al. |
| 4,724,137 A | 2/1988 | Hoppe et al. |
| 4,769,285 A | 9/1988 | Rasmussen |
| 4,806,338 A | 2/1989 | Smith |
| 4,806,345 A | 2/1989 | Bhattacharyya |
| 4,820,765 A | 4/1989 | Whyzmuzis |
| 4,822,601 A | 4/1989 | Goode et al. |
| 4,871,536 A | 10/1989 | Arraudeau et al. |
| 4,937,069 A | 6/1990 | Shin |
| 4,952,245 A | 8/1990 | Iwano et al. |
| 5,034,219 A | 7/1991 | Deshpande et al. |

(Continued)

FOREIGN PATENT DOCUMENTS

CA        1319306        6/1988

(Continued)

OTHER PUBLICATIONS

English language Derwent abstract of FR 2 816 506, May 2002.
International Search Report in PCT/US 01/47454, dated Aug. 29, 2002.
International Search Report in PCT/US 01/47499, dated Aug. 8, 2002.
Partial International Search Report in PCT/US 01/47497, dated Aug. 30, 2002.
English language Derwent abstract of EP 0 820 764 A1, Jan. 1998.
English language Derwent abstract of EP 0 923 928 A1, Jun. 1999.
English language Derwent abstract of EP 0 925 780 A1, Jun. 1999.
English language Derwent abstract of FR 2 811 552 A1, Jan. 2002.
Milan Jokić et al., *A Novel Type of Small Organic Gelators: Bis(Amino Acid) Oxalyl Amides*, 1995 J. Chem. Soc., Chem. Commun., 1723.
Kenji Hanabusa et al., *Prominent Gelation and Chiral Aggregation of Alkylamides Derived from trans-1,2-Diaminocyclohexane*, Angew. Chem. Int. Ed. Engl. 1996, 35, No. 17, 1949-1951.

(Continued)

*Primary Examiner* — Jyothsna Venkat

(74) *Attorney, Agent, or Firm* — Finnegan, Henderson, Farabow, Garrett & Dunner, LLP

(57) ABSTRACT

Compositions, in one embodiment a transfer resistant cosmetic composition, which may also be pliable and comfortable to wear upon application to a substrate. The compositions comprise, more particularly, at least one structuring polymer and at least one silicone resin. The invention, in one embodiment, relates to cosmetic, dermatological, and pharmaceutical products containing this composition.

4 Claims, No Drawings

U.S. PATENT DOCUMENTS

| | | | |
|---|---|---|---|
| 5,061,289 A | 10/1991 | Clausen et al. | |
| 5,069,897 A | 12/1991 | Orr | |
| 5,073,364 A | 12/1991 | Giezendanner et al. | |
| 5,075,103 A | 12/1991 | Halloran et al. | |
| 5,085,859 A * | 2/1992 | Halloran et al. | 424/70.121 |
| 5,102,656 A | 4/1992 | Kasat | |
| 5,126,136 A | 6/1992 | Merat et al. | |
| 5,166,355 A | 11/1992 | Leistner et al. | |
| 5,186,318 A | 2/1993 | Oestreich et al. | |
| 5,194,260 A | 3/1993 | Grollier et al. | |
| 5,196,260 A | 3/1993 | Dirshl et al. | |
| 5,223,559 A | 6/1993 | Arraudeau et al. | |
| 5,237,071 A | 8/1993 | Leistner et al. | |
| 5,252,323 A | 10/1993 | Richard et al. | |
| 5,268,029 A | 12/1993 | Demangeon et al. | |
| 5,272,241 A | 12/1993 | Lucarelli et al. | |
| 5,290,555 A | 3/1994 | Guthauser et al. | |
| 5,302,379 A | 4/1994 | Sojka | |
| 5,302,398 A | 4/1994 | Egidio et al. | |
| 5,342,894 A | 8/1994 | Robeson et al. | |
| 5,356,616 A | 10/1994 | Sojka | |
| 5,362,482 A | 11/1994 | Yoneyama et al. | |
| 5,372,852 A | 12/1994 | Titterington et al. | |
| 5,389,363 A * | 2/1995 | Snyder et al. | 424/70.7 |
| 5,436,006 A | 7/1995 | Hirose et al. | |
| 5,472,686 A | 12/1995 | Tsubaki et al. | |
| 5,486,431 A | 1/1996 | Tuttle et al. | |
| 5,489,431 A | 2/1996 | Ascione et al. | |
| 5,500,209 A | 3/1996 | Ross et al. | |
| 5,505,937 A * | 4/1996 | Castrogiovanni et al. | 424/64 |
| 5,510,452 A | 4/1996 | Santhanam | |
| 5,534,247 A | 7/1996 | Franjac et al. | |
| 5,536,871 A | 7/1996 | Santhanam | |
| 5,538,718 A | 7/1996 | Aul et al. | |
| 5,538,793 A | 7/1996 | Inokuchi et al. | |
| 5,540,853 A | 7/1996 | Trinh et al. | |
| 5,585,091 A | 12/1996 | Pelzer et al. | |
| 5,603,925 A | 2/1997 | Ross et al. | |
| 5,605,651 A | 2/1997 | Balzer | |
| 5,610,199 A | 3/1997 | Cohen et al. | |
| 5,612,043 A | 3/1997 | Deprez et al. | |
| 5,616,331 A | 4/1997 | Allard et al. | |
| 5,618,523 A | 4/1997 | Zysman et al. | |
| 5,620,693 A | 4/1997 | Piot et al. | |
| 5,645,632 A | 7/1997 | Pavlin | |
| 5,667,770 A | 9/1997 | Szweda et al. | |
| 5,679,357 A | 10/1997 | Dubief et al. | |
| 5,683,817 A | 11/1997 | Kenmochi | |
| 5,695,747 A | 12/1997 | Forestier et al. | |
| 5,702,519 A | 12/1997 | Nitta et al. | |
| 5,708,631 A | 1/1998 | Takenaka et al. | |
| 5,719,255 A | 2/1998 | Heucher et al. | |
| 5,733,537 A | 3/1998 | Halloran et al. | |
| 5,747,625 A | 5/1998 | Furukawa et al. | |
| 5,750,125 A | 5/1998 | Lahanas et al. | |
| 5,750,127 A | 5/1998 | Rokitowski | |
| 5,750,489 A | 5/1998 | Garcia et al. | |
| 5,769,902 A | 6/1998 | Samain | |
| 5,780,517 A | 7/1998 | Cohen et al. | |
| 5,783,657 A * | 7/1998 | Pavlin et al. | 528/310 |
| 5,795,565 A | 8/1998 | Eteve et al. | |
| 5,800,816 A | 9/1998 | Brieva et al. | |
| 5,807,968 A | 9/1998 | Heinrich et al. | |
| 5,825,543 A | 10/1998 | Ouderkirk et al. | |
| 5,830,444 A | 11/1998 | Miguel | |
| 5,830,447 A | 11/1998 | Hutchins et al. | |
| 5,830,483 A | 11/1998 | Seidel et al. | |
| 5,837,223 A | 11/1998 | Barone et al. | |
| 5,849,275 A | 12/1998 | Calello et al. | |
| 5,849,278 A | 12/1998 | Piot et al. | |
| 5,849,333 A | 12/1998 | Nordhauser et al. | |
| 5,849,909 A | 12/1998 | Richard et al. | |
| 5,851,517 A | 12/1998 | Mougin et al. | |
| 5,857,903 A | 1/1999 | Ramspeck et al. | |
| 5,858,338 A | 1/1999 | Piot et al. | |
| 5,866,149 A | 2/1999 | Piot et al. | |
| 5,871,758 A | 2/1999 | Nagy et al. | |
| 5,871,764 A | 2/1999 | Diaz et al. | |
| 5,874,069 A | 2/1999 | Mendolia et al. | |
| 5,882,363 A | 3/1999 | Spaulding et al. | |
| 5,891,424 A | 4/1999 | Bretzler et al. | |
| 5,897,869 A | 4/1999 | Roulier et al. | |
| 5,902,592 A | 5/1999 | Bara et al. | |
| 5,908,631 A | 6/1999 | Arnaud et al. | |
| 5,911,974 A | 6/1999 | Brieva et al. | |
| 5,919,441 A | 7/1999 | Mendolia et al. | |
| 5,925,337 A | 7/1999 | Arraudeau et al. | |
| 5,928,660 A | 7/1999 | Kabayashi et al. | |
| 5,945,085 A * | 8/1999 | Salas et al. | 424/45 |
| 5,945,095 A | 8/1999 | Mougin et al. | |
| 5,945,112 A | 8/1999 | Flynn et al. | |
| 5,955,060 A | 9/1999 | Huglin et al. | |
| 5,959,009 A | 9/1999 | Konik et al. | |
| 5,961,998 A | 10/1999 | Arnaud et al. | |
| 5,962,452 A | 10/1999 | Haase et al. | |
| 5,965,112 A | 10/1999 | Brieva et al. | |
| 5,972,095 A | 10/1999 | Graves et al. | |
| 5,972,354 A | 10/1999 | de la Poterie et al. | |
| 5,972,359 A | 10/1999 | Sine et al. | |
| 5,976,512 A | 11/1999 | Huber | |
| 5,976,514 A * | 11/1999 | Guskey et al. | 424/65 |
| 5,981,680 A | 11/1999 | Petroff et al. | |
| 5,985,298 A | 11/1999 | Brieva et al. | |
| 5,993,787 A | 11/1999 | Sun et al. | |
| 5,998,570 A | 12/1999 | Pavlin et al. | |
| 6,001,980 A | 12/1999 | Borzo et al. | |
| 6,004,567 A | 12/1999 | Marchi-Lemann et al. | |
| 6,007,796 A | 12/1999 | Menzel et al. | |
| 6,007,799 A | 12/1999 | Lee et al. | |
| 6,010,541 A | 1/2000 | de la Mettrie et al. | |
| 6,019,962 A | 2/2000 | Rabe et al. | |
| 6,036,947 A | 3/2000 | Barone et al. | |
| 6,042,815 A | 3/2000 | Kellner et al. | |
| 6,045,782 A * | 4/2000 | Krog et al. | 424/64 |
| 6,045,823 A | 4/2000 | Vollhardt et al. | |
| 6,051,216 A | 4/2000 | Barr et al. | |
| 6,054,517 A | 4/2000 | Spaulding et al. | |
| 6,060,072 A * | 5/2000 | Konik et al. | 424/401 |
| 6,063,398 A | 5/2000 | Gueret | |
| 6,066,328 A | 5/2000 | Ribier et al. | |
| 6,074,654 A | 6/2000 | Drechsler et al. | |
| 6,093,385 A | 7/2000 | Habeck et al. | |
| 6,103,249 A | 8/2000 | Roulier et al. | |
| 6,103,250 A | 8/2000 | Brieva et al. | |
| 6,106,820 A | 8/2000 | Morrissey et al. | |
| 6,111,055 A | 8/2000 | Berger et al. | |
| 6,126,929 A | 10/2000 | Mougin | |
| 6,132,745 A | 10/2000 | Marchi-lemann et al. | |
| 6,156,325 A | 12/2000 | Farer et al. | |
| 6,156,804 A | 12/2000 | Chevalier et al. | |
| 6,159,455 A | 12/2000 | Habeck et al. | |
| 6,165,454 A | 12/2000 | Patel et al. | |
| 6,165,971 A | 12/2000 | Oppenlander et al. | |
| 6,171,347 B1 | 1/2001 | Kunz | |
| 6,177,523 B1 | 1/2001 | Reich et al. | |
| 6,180,117 B1 * | 1/2001 | Berthiaume et al. | 424/401 |
| 6,180,123 B1 | 1/2001 | Mondet | |
| 6,190,673 B1 | 2/2001 | Guskey et al. | |
| 6,197,100 B1 | 3/2001 | Melbouchi | |
| 6,203,780 B1 | 3/2001 | Arnaud et al. | |
| 6,203,807 B1 | 3/2001 | Lemann | |
| 6,214,326 B1 | 4/2001 | Dupuis | |
| 6,214,329 B1 * | 4/2001 | Brieva et al. | 424/70.7 |
| 6,221,389 B1 | 4/2001 | Cannell et al. | |
| 6,224,851 B1 | 5/2001 | Bara | |
| 6,242,509 B1 | 6/2001 | Berger et al. | |
| 6,251,375 B1 | 6/2001 | Bara | |
| 6,251,409 B1 | 6/2001 | Hegyi et al. | |
| 6,254,876 B1 | 7/2001 | de la Poterie et al. | |
| 6,254,877 B1 | 7/2001 | de la Poterie et al. | |
| 6,264,933 B1 | 7/2001 | Bodelin et al. | |
| 6,268,466 B1 | 7/2001 | MacQueen et al. | |
| 6,280,846 B1 | 8/2001 | Darby et al. | |
| 6,287,552 B1 | 9/2001 | Tournilhac et al. | |
| 6,299,979 B1 | 10/2001 | Neubauer et al. | |
| 6,325,994 B1 | 12/2001 | Collin et al. | |
| 6,342,239 B1 | 1/2002 | Tachibana et al. | |

| | | |
|---|---|---|
| 6,348,563 B1 | 2/2002 | Fukuda et al. |
| 6,361,764 B2 | 3/2002 | Richard et al. |
| 6,372,235 B1 | 4/2002 | Livoreil et al. |
| 6,376,078 B1 | 4/2002 | Inokuchi |
| 6,383,502 B1 | 5/2002 | Dunshee et al. |
| 6,387,498 B1 | 5/2002 | Coulter et al. |
| 6,399,080 B1 | 6/2002 | Bara |
| 6,399,081 B1 | 6/2002 | Nakanishi et al. |
| 6,402,408 B1 * | 6/2002 | Ferrari ............ 401/64 |
| 6,410,003 B1 | 6/2002 | Bhatia et al. |
| 6,419,912 B1 | 7/2002 | Lezer |
| 6,423,306 B2 | 7/2002 | Caes et al. |
| 6,423,324 B1 | 7/2002 | Murphy et al. |
| 6,428,773 B1 | 8/2002 | Oko et al. |
| 6,432,391 B1 | 8/2002 | Bara |
| 6,447,759 B2 | 9/2002 | Noguchi et al. |
| 6,469,131 B2 | 10/2002 | Lawson et al. |
| 6,475,500 B2 | 11/2002 | Vatter et al. |
| 6,479,686 B2 | 11/2002 | Nakanishi et al. |
| 6,482,400 B1 | 11/2002 | Collin |
| 6,489,283 B1 | 12/2002 | Afriat |
| 6,491,931 B1 * | 12/2002 | Collin ............ 424/401 |
| 6,497,861 B1 | 12/2002 | Wang et al. |
| 6,503,521 B1 | 1/2003 | Atis et al. |
| 6,503,522 B2 | 1/2003 | Lawson et al. |
| 6,506,716 B1 | 1/2003 | Delplancke et al. |
| 6,524,598 B2 | 2/2003 | Sunkel et al. |
| 6,545,174 B2 | 4/2003 | Habeck et al. |
| 6,552,160 B2 | 4/2003 | Pavlin |
| 6,585,962 B2 | 7/2003 | Philippe et al. |
| 6,607,734 B1 | 8/2003 | Afriat |
| 6,649,173 B1 | 11/2003 | Arnaud et al. |
| 6,656,487 B2 | 12/2003 | Afriat et al. |
| 6,682,748 B1 | 1/2004 | De La Poterie et al. |
| 6,689,345 B2 | 2/2004 | Jager Lezer |
| 6,716,420 B2 | 4/2004 | Feng et al. |
| 6,726,917 B2 | 4/2004 | Kanji et al. |
| 6,749,173 B2 | 6/2004 | Heiling |
| 6,761,881 B2 | 7/2004 | Bara |
| 6,830,610 B1 | 12/2004 | Bruchert et al. |
| 6,835,399 B2 | 12/2004 | Collin |
| 6,852,326 B2 | 2/2005 | Breton |
| 6,869,594 B2 | 3/2005 | Ferrari |
| 6,875,245 B2 | 4/2005 | Pavlin |
| 6,881,400 B2 | 4/2005 | Collin |
| 6,960,339 B1 | 11/2005 | Ferrari |
| 6,979,469 B2 | 12/2005 | Ferrari et al. |
| 7,008,619 B2 | 3/2006 | Kanji |
| 7,008,629 B2 | 3/2006 | Kanji |
| 7,011,523 B2 | 3/2006 | Allred et al. |
| 7,011,823 B2 | 3/2006 | Ferrari et al. |
| 7,023,552 B2 | 4/2006 | Simon et al. |
| 7,025,953 B2 | 4/2006 | Blin et al. |
| 7,052,681 B2 | 5/2006 | Ferrari |
| 7,144,582 B1 | 12/2006 | Ferrari et al. |
| 7,276,547 B2 | 10/2007 | Pinzon et al. |
| 7,314,612 B2 | 1/2008 | Ferrari |
| 7,351,418 B2 | 4/2008 | Collin |
| 7,410,636 B2 | 8/2008 | Collin |
| 2001/0014312 A1 | 8/2001 | Nakanishi et al. |
| 2001/0014313 A1 | 8/2001 | Roulier et al. |
| 2001/0028887 A1 | 10/2001 | Douin et al. |
| 2001/0031280 A1 | 10/2001 | Ferrari et al. |
| 2001/0033846 A1 | 10/2001 | Roulier et al. |
| 2001/0036914 A1 | 11/2001 | Philippe et al. |
| 2002/0010179 A1 | 1/2002 | Richard et al. |
| 2002/0044918 A1 | 4/2002 | Bara |
| 2002/0058053 A1 | 5/2002 | Nakanishi et al. |
| 2002/0081323 A1 | 6/2002 | Nakanishi et al. |
| 2002/0102225 A1 | 8/2002 | Hess et al. |
| 2002/0107314 A1 | 8/2002 | Pinzon et al. |
| 2002/0111330 A1 | 8/2002 | Pinzon et al. |
| 2002/0114771 A1 | 8/2002 | Nakanishi |
| 2002/0114773 A1 | 8/2002 | Kanji et al. |
| 2002/0119171 A1 | 8/2002 | Gruning et al. |
| 2002/0120036 A1 | 8/2002 | Pinzon et al. |
| 2002/0122781 A1 | 9/2002 | Pinzon et al. |
| 2002/0131947 A1 | 9/2002 | Nakanishi |
| 2002/0141958 A1 | 10/2002 | Maio et al. |
| 2002/0150602 A1 | 10/2002 | Livoreil et al. |
| 2002/0159964 A1 | 10/2002 | Nakanishi et al. |
| 2002/0168335 A1 | 11/2002 | Collin |
| 2002/0172696 A1 | 11/2002 | Ferrari |
| 2002/0189030 A1 | 12/2002 | Collin |
| 2002/0192168 A1 | 12/2002 | Blin et al. |
| 2003/0012764 A1 | 1/2003 | Collin |
| 2003/0026772 A1 | 2/2003 | Jager-Lezer et al. |
| 2003/0044367 A1 | 3/2003 | Simon et al. |
| 2003/0086883 A1 | 5/2003 | Feng et al. |
| 2003/0129211 A9 | 7/2003 | Livoreil et al. |
| 2003/0147837 A1 | 8/2003 | Cavazzuti et al. |
| 2003/0161807 A1 | 8/2003 | Lemann |
| 2003/0161848 A1 | 8/2003 | Ferrari et al. |
| 2003/0185780 A1 | 10/2003 | Ferrari et al. |
| 2003/0198613 A1 | 10/2003 | Feng et al. |
| 2004/0013625 A1 | 1/2004 | Kanji |
| 2004/0028636 A1 | 2/2004 | Collin |
| 2004/0042980 A1 | 3/2004 | Kanji et al. |
| 2004/0086478 A1 | 5/2004 | Ferrari |
| 2004/0091510 A1 | 5/2004 | Feng et al. |
| 2004/0126401 A1 | 7/2004 | Collin |
| 2004/0156813 A2 | 8/2004 | Ferrari |
| 2004/0166076 A1 | 8/2004 | Ferrari et al. |
| 2004/0166133 A1 | 8/2004 | Cavazzuti et al. |
| 2004/0223987 A1 | 11/2004 | Ferrari |
| 2004/0247549 A1 | 12/2004 | Lu et al. |
| 2005/0008595 A1 | 1/2005 | Duffournier et al. |
| 2005/0008598 A1 | 1/2005 | Lu et al. |
| 2005/0008599 A1 | 1/2005 | Lu et al. |
| 2005/0019285 A1 | 1/2005 | Lee et al. |
| 2005/0065261 A1 | 3/2005 | Darlington, Jr. et al. |
| 2005/0089491 A1 | 4/2005 | Collin |
| 2005/0089505 A1 | 4/2005 | Collin |
| 2005/0089541 A1 | 4/2005 | Lacoutiere |
| 2005/0118122 A1 | 6/2005 | Simon et al. |
| 2005/0191327 A1 | 9/2005 | Yu et al. |
| 2006/0257336 A1 | 11/2006 | Ferrari et al. |

FOREIGN PATENT DOCUMENTS

| | | |
|---|---|---|
| CA | 2003346 | 5/1990 |
| CA | 1319306 | 6/1993 |
| DE | 38 39 136 A1 | 5/1990 |
| DE | 38 43 892 A | 6/1990 |
| DE | 38 43 892 A1 | 6/1990 |
| DE | 42 08 297 A | 9/1993 |
| DE | 42 08 297 A1 | 9/1993 |
| DE | 42 34 886 A | 4/1994 |
| DE | 42 34 886 A1 | 4/1994 |
| DE | 195 43 988 A | 5/1997 |
| DE | 195 43 988 A1 | 5/1997 |
| DE | 197 07 309 A1 | 8/1998 |
| DE | 197 26 184 A1 | 12/1998 |
| DE | 197 50 246 A1 | 5/1999 |
| DE | 198 55 649 A1 | 6/2000 |
| DE | 199 51 010 A | 4/2001 |
| DE | 199 51 010 A1 | 4/2001 |
| EP | 0 169 997 B1 | 2/1986 |
| EP | 0 295 886 | 12/1988 |
| EP | 0 295 886 B1 | 12/1988 |
| EP | 0 370 470 A2 | 5/1990 |
| EP | 0 370 470 B1 | 5/1990 |
| EP | 0 374 332 A1 | 6/1990 |
| EP | 0 412 710 A2 | 2/1991 |
| EP | 0 412 710 B1 | 2/1991 |
| EP | 0 444 633 A2 | 9/1991 |
| EP | 0 462 709 A2 | 12/1991 |
| EP | 0 507 692 A1 | 10/1992 |
| EP | 0 517 104 B1 | 12/1992 |
| EP | 0 518 772 A1 | 12/1992 |
| EP | 0 518 773 A1 | 12/1992 |
| EP | 0 557 196 A1 | 8/1993 |
| EP | 0 570 838 B1 | 11/1993 |
| EP | 0 600 445 A2 | 6/1994 |
| EP | 0 602 905 B1 | 6/1994 |
| EP | 0 609 132 B1 | 8/1994 |
| EP | 0 623 670 A2 | 11/1994 |
| EP | 0 628 582 B1 | 12/1994 |
| EP | 0 669 323 A1 | 8/1995 |

| | | | | | | |
|---|---|---|---|---|---|---|
| EP | 0 673 642 | B1 | 9/1995 | FR | 2 804 018 | 7/2001 |
| EP | 0 708 114 | A1 | 4/1996 | FR | 2 804 286 | 8/2001 |
| EP | 0 749 746 | A1 | 12/1996 | FR | 2 810 562 | 12/2001 |
| EP | 0 749 747 | A1 | 12/1996 | FR | 2 811 225 | 1/2002 |
| EP | 0 749 748 | A | 12/1996 | FR | 2 811 552 A1 | 1/2002 |
| EP | 0 749 748 | A1 | 12/1996 | FR | 2 816 506 | 5/2002 |
| EP | 0 775 483 | A1 | 5/1997 | FR | 2 817 739 | 6/2002 |
| EP | 0 775 698 | A1 | 5/1997 | FR | 2 817 740 | 6/2002 |
| EP | 0 790 243 | A1 | 8/1997 | FR | 2 817 742 | 6/2002 |
| EP | 0 796 851 | A1 | 9/1997 | FR | 2 817 743 | 6/2002 |
| EP | 0 797 976 | A2 | 10/1997 | FR | 2 819 399 | 7/2002 |
| EP | 0 820 764 | A1 | 1/1998 | FR | 2 819 400 | 7/2002 |
| EP | 0 847 752 | A1 | 6/1998 | FR | 2 819 402 | 7/2002 |
| EP | 0 863 145 | A2 | 9/1998 | FR | 2 848 822 A1 | 6/2004 |
| EP | 0 877 063 | B1 | 11/1998 | GB | 1 117 129 | 6/1968 |
| EP | 0 878 469 | A1 | 11/1998 | GB | 1 194 901 | 6/1970 |
| EP | 0 879 592 | A2 | 11/1998 | GB | 1 194 902 | 6/1970 |
| EP | 0 887 073 | A1 | 12/1998 | GB | 1 220 069 | 1/1971 |
| EP | 0 893 119 | B1 | 1/1999 | GB | 1 273 004 | 5/1972 |
| EP | 0 923 928 | A1 | 6/1999 | GB | 1 444 204 | 7/1976 |
| EP | 0 925 780 | A1 | 6/1999 | GB | 1 539 625 | 1/1979 |
| EP | 0 928 608 | A2 | 7/1999 | GB | 2 014 852 | 9/1979 |
| EP | 0 930 058 | B1 | 7/1999 | GB | 2 021 411 A | 12/1979 |
| EP | 0 930 060 | A1 | 7/1999 | GB | 2 147 305 A | 5/1985 |
| EP | 0 933 376 | A2 | 8/1999 | GB | 2 196 978 A | 5/1988 |
| EP | 0 943 340 | A1 | 9/1999 | JP | 45-41318 | 12/1970 |
| EP | 0 958 804 | A2 | 11/1999 | JP | 48-38861 | 11/1973 |
| EP | 0 958 805 | A2 | 11/1999 | JP | 49-75740 | 7/1974 |
| EP | 0 958 811 | A1 | 11/1999 | JP | 50/58242 | 5/1975 |
| EP | 0 959 066 | A2 | 11/1999 | JP | 52-007067 | 2/1977 |
| EP | 0 959 091 | A1 | 11/1999 | JP | 53043577 A | 4/1978 |
| EP | 0 967 200 | A1 | 12/1999 | JP | 56123909 A | 9/1981 |
| EP | 0 976 390 | A1 | 2/2000 | JP | 56166276 A | 12/1981 |
| EP | 0 984 025 | A2 | 3/2000 | JP | 61065809 A | 4/1986 |
| EP | 1 002 514 | A1 | 5/2000 | JP | 62/061911 | 3/1987 |
| EP | 1 018 332 | | 7/2000 | JP | 62061911 | 3/1987 |
| EP | 1 031 342 | A1 | 8/2000 | JP | 10 67618 | 3/1989 |
| EP | 1 044 676 | A2 | 10/2000 | JP | 64-90110 | 4/1989 |
| EP | 1 048 282 | A1 | 11/2000 | JP | 2127568 A | 5/1990 |
| EP | 1 053 742 | A1 | 11/2000 | JP | 02/200612 | 8/1990 |
| EP | 1 062 944 | A1 | 12/2000 | JP | 02-207014 | 8/1990 |
| EP | 1 062 959 | A1 | 12/2000 | JP | 2216279 A | 8/1990 |
| EP | 1 064 919 | A1 | 1/2001 | JP | 3014683 A | 1/1991 |
| EP | 1 064 920 | A1 | 1/2001 | JP | 4 230312 | 8/1992 |
| EP | 1 066 814 | A1 | 1/2001 | JP | 04/230312 | 8/1992 |
| EP | 1 068 854 | A1 | 1/2001 | JP | 04346909 A | 12/1992 |
| EP | 1 068 855 | | 1/2001 | JP | 5-17710 | 1/1993 |
| EP | 1 068 855 | A1 | 1/2001 | JP | 6 299075 | 10/1994 |
| EP | 1 068 856 | | 1/2001 | JP | 7-89826 | 4/1995 |
| EP | 1 068 856 | A1 | 1/2001 | JP | 7179795 A | 7/1995 |
| EP | 1 086 945 | A1 | 3/2001 | JP | 7-258460 | 10/1995 |
| EP | 1 090 627 | B1 | 4/2001 | JP | 7267827 A | 10/1995 |
| EP | 1 095 959 | A2 | 5/2001 | JP | 8225316 A | 9/1996 |
| EP | 1 114 636 | | 7/2001 | JP | 9/20631 | 1/1997 |
| EP | 1 114 636 | A1 | 7/2001 | JP | 09-020631 | 1/1997 |
| EP | 1 213 011 | A1 | 6/2002 | JP | 9-188830 | 7/1997 |
| EP | 1 213 316 | A2 | 6/2002 | JP | 09/255560 | 9/1997 |
| EP | 1 382 322 | A2 | 1/2004 | JP | 09-263516 | 10/1997 |
| EP | 1 477 154 | A1 | 11/2004 | JP | 9295922 A | 11/1997 |
| EP | 1 343 459 | B1 | 1/2007 | JP | 10-001444 | 1/1998 |
| EP | 1 359 886 | B1 | 3/2007 | JP | 10/007527 | 1/1998 |
| FR | 1 529 329 | | 5/1968 | JP | 10-007527 | 1/1998 |
| FR | 2 232 303 | | 3/1975 | JP | 10/120903 | 5/1998 |
| FR | 2 315 991 | | 1/1977 | JP | 10-158450 | 6/1998 |
| FR | 2 416 008 | | 8/1979 | JP | 10-158451 | 6/1998 |
| FR | 2 528 699 | | 12/1983 | JP | 10-175816 | 6/1998 |
| FR | 2 659 011 | | 9/1991 | JP | 10-506643 | 6/1998 |
| FR | 2 674 126 | | 9/1992 | JP | 10/212213 | 8/1998 |
| FR | 2 785 179 | | 5/2000 | JP | 10/251118 | 9/1998 |
| FR | 2 791 558 | | 10/2000 | JP | 10-251118 | 9/1998 |
| FR | 2 796 270 | | 1/2001 | JP | 10259344 A | 9/1998 |
| FR | 2 796 271 | | 1/2001 | JP | 10-306012 | 11/1998 |
| FR | 2 796 272 | | 1/2001 | JP | 11106216 A | 4/1999 |
| FR | 2 796 273 | | 1/2001 | JP | 11 236314 | 8/1999 |
| FR | 2 796 276 | | 1/2001 | JP | 11/335228 | 12/1999 |
| FR | 2 796 550 | | 1/2001 | JP | 11/335242 | 12/1999 |
| FR | 2 802 806 | | 6/2001 | JP | 11/335254 | 12/1999 |
| FR | 2 804 014 | | 7/2001 | JP | 2000038314 A | 2/2000 |
| FR | 2 804 017 | | 7/2001 | JP | 2000038316 A | 2/2000 |

| | | | |
|---|---|---|---|
| JP | 2000038317 A | 2/2000 | |
| JP | 2000038321 A | 2/2000 | |
| JP | 2000-503305 | 3/2000 | |
| JP | 2000086427 A | 3/2000 | |
| JP | 2000086429 A | 3/2000 | |
| JP | 2000086438 A | 3/2000 | |
| JP | 2000-0154112 | 6/2000 | |
| JP | 2001-011340 | 1/2001 | |
| JP | 2001-502742 | 2/2001 | |
| JP | 2001-081320 | 3/2001 | |
| JP | 2001-206821 | 7/2001 | |
| JP | 2002-539220 | 11/2002 | |
| JP | 2004-517906 | 6/2004 | |
| WO | WO 86/04916 | 8/1986 | |
| WO | WO 87/03783 | 7/1987 | |
| WO | WO 91/12793 | 9/1991 | |
| WO | WO 93/04665 | 3/1993 | |
| WO | WO 93/21763 | 11/1993 | |
| WO | WO 93/23008 | 11/1993 | |
| WO | WO 94/18261 | 8/1994 | |
| WO | WO 94/21233 | 9/1994 | |
| WO | WO 95/15741 | 6/1995 | |
| WO | WO 95/24887 | 9/1995 | |
| WO | WO 95/33000 | 12/1995 | |
| WO | WO 96/15761 | 5/1996 | |
| WO | WO 96/38126 | 5/1996 | |
| WO | WO 96/40044 | 12/1996 | |
| WO | WO 97/17057 | 5/1997 | |
| WO | WO 97/36573 | 10/1997 | |
| WO | WO 98/17243 | 4/1998 | |
| WO | WO 98/17705 | 4/1998 | |
| WO | WO 98/22078 | 5/1998 | |
| WO | WO 98/25922 | 6/1998 | |
| WO | WO 98/27162 | 6/1998 | |
| WO | WO 98/42298 | 10/1998 | |
| WO | WO 98/47470 | 10/1998 | |
| WO | WO 98/52534 | 11/1998 | |
| WO | WO 98/58623 | 12/1998 | |
| WO | WO 99/24002 | 5/1999 | |
| WO | WO 99/36477 | 7/1999 | |
| WO | WO 99/43297 | 9/1999 | |
| WO | WO 99/66888 | 12/1999 | |
| WO | WO 00/06114 | 2/2000 | |
| WO | WO 00/27350 | 5/2000 | |
| WO | WO 00/40216 | 7/2000 | |
| WO | WO 00/61080 | 10/2000 | |
| WO | WO 00/61081 | 10/2000 | |
| WO | WO 00/74519 A2 | 12/2000 | |
| WO | WO 01/51020 | 7/2001 | |
| WO | WO 01/52799 | 7/2001 | |
| WO | WO 01/97758 A2 | 12/2001 | |
| WO | WO 01/97773 | 12/2001 | |
| WO | WO 01/97773 A1 | 12/2001 | |
| WO | WO 02/03932 A2 | 1/2002 | |
| WO | WO 02/03935 A2 | 1/2002 | |
| WO | WO 02/03950 A2 | 1/2002 | |
| WO | WO 02/03951 A2 | 1/2002 | |
| WO | WO 02/47605 A2 | 6/2002 | |
| WO | WO 02/47608 A2 | 6/2002 | |
| WO | WO 02/47619 A2 | 6/2002 | |
| WO | WO 02/47620 | 6/2002 | |
| WO | WO 02/47622 A2 | 6/2002 | |
| WO | WO 02/47627 A1 | 6/2002 | |
| WO | WO 02/47629 A1 | 6/2002 | |
| WO | WO 02/47630 A1 | 6/2002 | |
| WO | WO 02/47658 | 6/2002 | |
| WO | WO 02/49583 A1 | 6/2002 | |
| WO | WO 02/49601 | 6/2002 | |
| WO | WO 02/055030 A2 | 7/2002 | |
| WO | WO 02/055031 A1 | 7/2002 | |
| WO | WO 02/056845 A1 | 7/2002 | |
| WO | WO 02/056847 A1 | 7/2002 | |
| WO | WO 02/056848 A1 | 7/2002 | |
| WO | WO 02/058642 | 8/2002 | |
| WO | WO 02/092047 A1 | 11/2002 | |
| WO | WO 02/092663 A1 | 11/2002 | |
| WO | WO 02/102322 A2 | 12/2002 | |
| WO | WO 2005/013887 A2 | 2/2005 | |

OTHER PUBLICATIONS

Toshimi Shimizu et al., *Stereochemical Effect of Even-Odd Connecting Links on Supramolecular Assemblies Made of 1-Glucosamide Bolaamphiphiles*, J. Am Chem. Soc. 1997, 119, 2812-2818.

Kenji Hanabusa et al., *Terephthaloyl Derivatives as New Gelators; Excellent Gelation Ability and Remarkable Increase of Gel Strength by Adding Polymers*, 1999 Chemistry Letters 767.

Xuzhong Luo et al., *Self-assembled organogels formed by monoalkyl derivatives of oxamide*, 2000 Chem. Commun. 2091-92.

Kenji Hanabusa et al., *Easy Preparation and Gelation of New Gelator Based on L-Lysine*, 2000 Chemistry Letters, 1070.

Co-Pending U.S. Appl. No. 09/749,036; Title: Composition Comprising at Least One Hetero Polymer and at Least One Pasty Fatty Substance and Methods for Use Inventors: Véronique Ferrari et al. filed Dec. 28, 2000.

PCT Application No. PCT/US01/47459; Title: Cosmetic Compositions Containing At Least One Heteropolymer and At Least One Film-Forming Silicone Resin and Methods of Using Inventors: Mohamed Kanji et al. U.S. Filing Date: Dec. 12, 2001.

PCT Application No. PCT/US01/47499; Title: Cosmetic Compositions Containing Heteropolymers and Oil-Soluble Cationic Surfactants and Methods of Using Same Inventors: Carlos Pinzon and Paul Thau U.S. Filing Date: Dec. 12, 2001.

PCT Application No. PCT/FR01/03965; Title Cosmetic Composition Comprising Hetero Polymers and a Solid Substance and Method of Using Same Inventors: Roberto Cavazzuti et al. International Filing Date: Dec. 12, 2001.

PCT Application No. PCT/US01/47454; Title: Compositions Containing Heteropolymers and Oil-Soluble Polymers and Methods of Using Same Inventors: Carlos Pinzon and Paul Thau U.S. Filing Date: Dec. 12, 2001.

PCT Application No. PCT/US01/47497; Title: Compositions Containing Heteropolymers and Oil-Soluble Esters and Methods of Using Same Inventors: Carlos Pinzon and Paul Thau U.S. Filing Date: Dec. 12, 2001.

PCT Application No. PCT/US01/47496; Title: Compositions Containing Heteropolymers and Methods of Using Same Inventors: Carlos Pinzon and Paul Thau U.S. Filing Date: Dec. 12, 2001.

PCT Application No. PCT/FR01/03962; Title: Wax-Free Cosmetic Composition Structured in Rigid Form With a Polymer Inventors: Véronique Ferrari et al. International Filing Date: Dec. 12, 2001.

PCT Application No. PCT/FR01/03963; Title: Wax-Free Cosmetic Composition Structured in Rigid Form With a Polymer Inventor: Véronique Ferrari International Filing Date: Dec. 12, 2001.

Co-Pending Application No. unassigned; Title: Cosmetic Compositions Containing at Least One Heteropolymer and at Least One Organogelator U.S. Filing Date: May 3, 2002.

Charles M. Hansen, "*The Three Dimensional Solubility Parameter—Key to Paint Component Affinities: I. Solvents, Plasticizers, Polymers, and Resins*," Journal of Paint Technology, vol. 39, No. 505, Feb. 1967, pp. 104-117.

Yasuda et al., *Novel Low-molecular-weight Organic Gels: N,N', N"-Tristearyltrimesamide/Organic Solvent System*, Chemistry Letters, pp. 575-576, 1996, the month of publication is not available.

Bush Boake Allen, Inc., *Uniclear Formulations*, dated Oct. 13, 1998.

PCT Application No. PCT/IB01/02780; Title: Cosmetic Compositions Containing At Least One Heteropolymer and At Least One Organogelator International Filing Date: Dec. 12, 2001.

Co-Pending U.S. Appl. No. 09/971,028, Title: Methods of Dispersing At Least One Coloring Agent Using At Least One Heteropolymer filed Oct. 5, 2001.

Co-Pending U.S. Appl. No. 10/198,931, Title: Composition Comprising At Least One Heteropolymer and Fibers, and Methods of Using the Same filed Jul. 22, 2002.

Co-Pending U.S. Appl. No. 09/937,314; Title: A Transfer-Free Composition Comprising At Least One Fatty Phase That Is Structured With At Least One Polymer filed Sep. 24, 2001.

Co-Pending U.S. Appl. No. 10/129,377; Title: Cosmetic Compositions Comprising a Polymer Blend filed Dec. 11, 2001.

Co-Pending U.S. Appl. No. 10/012,051; Title: Use of a Polymer for Obtaining an Express Make-Up of Keratin Materials filed Dec. 11, 2001.

Co-Pending U.S. Appl. No. 10/012,052; Title: Cosmetic Composition Comprising a Wax and a Polymer Inventors: Nathalie Collin filed Dec. 11, 2001.
Co-Pending U.S. Appl. No. 10/046,568; Title: Nail Polish Composition Comprising a Polymer filed Jan. 16, 2002.
Co-Pending U.S. Appl. No. 10/047,987, Title: Cosmetic Composition Containing a Polymer and a Fluoro Oil filed Jan. 17, 2002.
Co-Pending U.S. Appl. No. 10/312,083 Title: Solid Emulsion Containing a Liquid Fatty Phase Structured With a Polymer filed Dec. 23, 2002.
Co-Pending U.S. Appl. No. 10/203,375, Title: Transparent or Translucent Colored Cosmetic Composition filed Aug. 9, 2002.
Co-Pending U.S. Appl. No. 10/203,374, Title: Method for Making a Coloured Make-Up Cosmetic Composition With Controlled Transmittance filed Aug. 9, 2002.
English language Derwent abstract of DE 195 43 988.
English language Derwent abstract of DE 199 51 010.
English language Derwent abstract of DE 38 43 892.
English language Derwent abstract of DE 42 08 297.
English language Derwent abstract of DE 42 34 886.
English language Derwent abstract of EP 0 169 997 B2.
English language Derwent abstract of EP 0 749 748.
English language Derwent abstract of FR 2 796 272.
English language Derwent abstract of FR 2 796 273.
English language Derwent abstract of FR 2 804 017.
English language Derwent abstract of FR 2 804 018.
English language Derwent abstract of FR 2 810 562.
English language Derwent abstract of FR 2 811 225.
English language Derwent abstract of FR 2 817 739.
English language Derwent abstract of FR 2 817 740.
English language Derwent abstract of Fr 2 817 743.
English language Derwent abstract of FR 2 819 399.
English language Derwent abstract of FR 2 819 400.
English language Derwent abstract of JP 10/120903.
English language Derwent abstract of JP 11/335228.
English language Derwent abstract of JP 11/335242.
English language Derwent abstract of JP 11/335254.
English language Derwent abstract of JP 2000038314 A.
English language Derwent abstract of JP 2000038316 A and JP 2000038317 A.
English language Derwent abstract of JP 2000038321 A.
English language Derwent abstract of JP 2000086427 A.
English language Derwent abstract of JP 2000086429 A.
English language Derwent abstract of JP 2000086438 A.
English language Derwent abstract of JP 920631.
Handbook of Cosmetic Science and Tech. Elsevier Advanced Tech., 1st Edition (1994), p. 19.
International Search Report in PCT/FR01/03726, dated Apr. 18, 2002.
Kirk-Othmer, "Encyclopedia of Chemical Technology", Third Edition, vol. 22, John Wiley & Sons, 1983, pp. 332-342.
PCT Application No. PCT/US03/41618; Title: Cosmetic Compositions Comprising a Structuring Agent, Silicone Powder and Swelling Agent Inventor: Shao Xiang Lu, Terry Van Liew, Nathalie Geffroy-Hyland International Filing Date: Dec. 22, 2003.
PCT Application No. PCT/US04/01071; Title: Long Wear Cosmetic Composition Inventor: Balanda Atis International Filing Date: Jan. 16, 2004.
English language Derwent abstract of EP 0 976 390 A1.
English language Derwent abstract of EP 1 002 514 A1.
English language Derwent abstract of EP 1 031 342 A1.
English language Derwent abstract of EP 1 048 282 A1.
English language Derwent abstract of EP 1 053 742 A1.
English language Derwent abstract of EP 1 064 919 A1.
English language Derwent abstract of EP 1 064 920 A1.
English language Derwent abstract of EP 1 066 814 A1.
English language Derwent abstract of EP 1 068 854 A1.
English language Derwent abstract of EP 1 068 855 A1.
English language Derwent abstract of EP 1 068 856 A1.
English language Derwent abstract of EP 1 086 945 A1.
English language Derwent abstract of EP 1 090 627 A1.
English language Derwent abstract of EP 1 114 636 A1.
English language Derwent abstract of FR 2 232 303.
English language Derwent abstract of FR 2 674 126.
English language Derwent abstract of FR 2 785 179.
English language Derwent abstract of FR 2 796 270.
English language Derwent abstract of FR 2 796 271.
English language Derwent abstract of FR 2 796 276.
English language Derwent abstract of FR 2 802 806.
English language Derwent abstract of FR 2 819 402.
English language Derwent abstract of JP 02/200612.
English language Derwent abstract of JP 04/346909.
English language Derwent abstract of JP 09/255560.
English language Derwent abstract of JP 10/007527.
English language Derwent abstract of JP 10/212213.
English language Derwent abstract of JP 10/259344.
English language Derwent abstract of JP 11/106216.
English language Derwent abstract of JP 2/127568.
English language Derwent abstract of JP 2/216279.
English language Derwent abstract of JP 3/014683.
English language Derwent abstract of JP 61/065809.
English language Derwent abstract of JP 62/061911.
English language Derwent abstract of JP 7/179795.
English language Derwent abstract of JP 7/267827.
English language Derwent abstract of JP 8/225316.
English language Derwent abstract of JP 9/295922.
English language Derwent abstract of WO 01/97773.
English language Derwent abstract of WO 02/056847.
English language Derwent abstract of WO 02/056848.
English language Derwent abstract of WO 02/47622.
English language Derwent abstract of WO 02/47629.
English language Derwent abstract of WO 02/47630.
English language Derwent abstract of Wo 86/04916.
Estee Lauder MagnaScopic Maximum Volume mascara product packaging, believed to have first been sold in 2003.
Estee Lauder's Response to Plaintiffs First Set of Interrogatories (Nos. 1-6), dated Sep. 27, 2004, in the on-going litigation *L'Oreal S.A., et al. v. The Estee Lauder Companies Inc. et al.*, Civil Action No. 04-1660 (D.C.N.J.).
French Search Report in FR 0000920 (priority document for PCT/FR01/00229), dated Nov. 10, 2000.
French Search Report in FR 0001004, dated Nov. 10, 2000.
French Search Report in FR 0008084, dated Mar. 28, 2001.
French Search Report in FR 0008913, dated Mar. 20, 2001.
French Search Report in FR 0016161, dated Sep. 6, 2001.
French Search Report in FR 0016163, dated Aug. 1, 2001.
Estee Lauder's Amended Answer and Counterclaims, dated Apr. 21, 2005, in the ongoing litigation *L'Oreal S.A., et al., v. The Estee Lauder Companies Inc., et al.*, Civil Action No. 04-1660 (D.N.J.).
Estee Lauder's Response to Plaintiffs Third Set of Interrogatories (Nos. 8-13), dated Jun. 21, 2005, in the on-going litigation *L'Oreal S.A., et al. v. The Estee Lauder Companies Inc., et al.*, Civil Action No. 04-1660 (D.N.J.).
Office Action in co-pending U.S. Appl. No. 09/733,898 dated Apr. 25, 2005.
Office Action in co-pending U.S. Appl. No. 09/733,900, dated Jun. 2, 2005.
Office Action in co-pending U.S. Appl. No. 09/733,896, dated Jul. 13, 2005.
Office Action in co-pending U.S. Appl. No. 09/749,036 dated Apr. 29, 2005.
Office Action in co-pending U.S. Appl. No. 10/012,052, dated Jun. 3, 2005.
Office Action in co-pending U.S. Appl. No. 10/203,254 dated Apr. 22, 2005.
Office Action in co-pending U.S. Appl. No. 10/203,375, dated May 13, 2005.
Office Action in co-pending U.S. Appl. No. 10/312,083 dated Apr. 18, 2005.
Office Action in co-pending U.S. Appl. No. 10/699,780, dated Jun. 15, 2005.
Office Action in co-pending U.S. Appl. No. 10/746,612 dated Jun. 15, 2005.
Richard J. Lewis, Sr., "Ricinoleic Acid," Hawley's Condensed Chemical Dictionary 972 (13th. 1997).
English language Derwent abstract of JP A 62061911.

English language Derwent abstract of EP 0 943 340 A1.
P. Terech, "Low-Molecular Weight Organogelators," in *Specialist Surfactants*, ch. 8, pp. 208-268 (I.D. Robb, ed., 1997).
Co-Pending U.S. Appl. No. 09/733,900; Title: Cosmetic Compositions Containing Heteropolymers and Oil-Soluble Cationic Surfactants and Methods of Using Inventors: Carlos Pinzon and Paul Thau filed Dec. 12, 2000.
Co-Pending U.S. Appl. No. 09/618,066; Title: Compositions in Rigid Form Structured With a Polymer Inventors: Veronique Ferrari and Pascal Simon filed Jul. 17, 2000.
Co-Pending U.S. Appl. No. 09/685,577; Title: Compositions in Rigid Form Structured With a Polymer Inventors: Véronique Ferrari and Pascal Simon filed Oct. 11, 2000.
Co-Pending U.S. Appl. No. 11/351,309, Title: Cosmetic Composition Containing a Polymer and a Fluoro Oil, filed Feb. 10, 2006.
Co-Pending U.S. Appl. No. 11/406,371; Title: Cosmetic Composition Comprising Silica Particles, Reflecting Particles, and At Least One Polymer, Preparative Process, and Uses Thereof, filed Apr. 19, 2006.
English language esp@cenet abstract of DE 195 43 988 A1.
English language Derwent Abstract of DE 197 26 184 A1.
English language Derwent abstract of DE 197 50 246 A1.
English language Derwent abstract of DE 198 55 649 A1.
English language Derwent abstract of EP 0 507 692 A1.
English language Derwent abstract of EP 0 518 772 A1.
English language Derwent abstract of EP 0 518 773 A1.
English language Derwent abstract of EP 0 669 323 A1.
English language Derwent abstract of EP 0 775 698 A1.
English language Derwent abstract of EP 0 790 243 A1.
English language Derwent abstract of EP 0 863 145 A2.
English language Derwent abstract of EP 0 878 469 A1.
English language Derwent abstract of EP 0 967 200 A1.
English language Derwent abstract of EP 1 068 855.
English language esp@cenet abstract of EP 1 068 856.
English language esp@cenet abstract of EP 1 114 636.
English language esp@cenet abstract of EP 1 343 459.
English language esp@cenet abstract of EP 1 382 322 A2.
English language esp@cenet abstract for EP 1 477 154 A1.
English language Derwent abstract of FR 2 315 991.
English language Derwent abstract of FR 2 416 008.
English language Derwent abstract of FR 2 528 699.
English language Derwent abstract of FR 2 796 550.
English language Derwent abstract of FR 2,804,286.
English Language esp@cenet abstract of FR 2 817 742.
English Language Derwent Abstract of FR 2 804 014.
English language esp@cenet abstract of FR 2 848 822 A1.
English language esp@cenet abstract of JP 02-207014.
English language Abstract from Patent Abstracts of Japan for JP 09-020631.
English language Derwent Abstract for JP 9-188830.
English language Derwent abstract for JP 09-263516.
English language esp@cenet abstract for JP 10-001444.
English language esp@cenet Abstract of JP 10-306012.
English language Derwent Abstract for JP 10-158450.
English language Derwent Abstract for JP 10-158451.
English language Derwent Abstract for JP 10-506643.
English language esp@cenet abstract for JP 10-67618.
English language esp@cenet abstract for JP 10-007527.
English language esp@cenet Abstract of JP 10-251118.
English language esp@cenet Abstract of JP 11-236314.
English language esp@cenet abstract for JP2000-154112.
English language esp@cenet abstract for JP2000-503305.
English language esp@cenet Abstract for JP 2001-011340.
English language esp@cenet abstract for JP 2002/539220 (WO0055264).
English language Derwent abstract for JP 45-41318.
English language Derwent abstract for JP 48-38861.
English language Derwent abstract for JP 49-75740.
English language esp@cenet Abstract of JP 4 230312.
English language Derwent Abstract for JP 5-17710.
English language esp@cenet abstract for JP 52-007067.
English language esp@cenet Abstract for JP 6-299075.
Co-pending U.S. Appl. No. 10/747,412 dated Feb. 20, 2008.
Office Action in co-pending U.S. Appl. No. 09/685,578 dated Jul. 30, 2007.
Office Action in co-pending U.S. Appl. No. 09/685,578 dated Apr. 7, 2008.
Office Action in co-pending U.S. Appl. No. 09/685,578 dated Aug. 28, 2008.
Office Action in co-pending U.S. Appl. No. 09/733,897 dated Feb. 7, 2008.
Office Action in co-pending U.S. Appl. No. 10/466,166 dated Feb. 7, 2008.
Office Action in co-pending U.S. Appl. No. 10/918,579 dated May 21, 2008.
Office Action in co-pending U.S. Appl. No. 10/918,579, dated Jan. 25, 2008.
Office Action in co-pending U.S. Appl. No. 11/212,811 dated Mar. 21, 2008.
English language Abstract for JP 2000-063674.
English Language Abstract for JP 2003-055155.
Office Action in co-pending U.S. Appl. No. 10/012,052 dated Mar. 6, 2009.
Office Action in co-pending U.S. Appl. No. 10/466,166 dated Apr. 1, 2009.
Office Action in co-pending U.S. Appl. No. 09/749,036 dated Mar. 6, 2009.
Office Action in co-pending U.S. Appl. No. 10/747,412 dated Jun. 10, 2009.
Office Action in co-pending U.S. Appl. No. 09/733,897 dated Jun. 23, 2009.
Office Action in co-pending U.S. Appl. No. 09/733,900 dated May 1, 2009.
Office Action in co-pending U.S. Appl. No. 10/494,864 dated Mar. 6, 2009.
Office Action in co-pending U.S. Appl. No. 10/746,612 dated Jul. 22, 2009.
Office Action in co-pending Application No. 10/699,780 dated Aug. 18, 2009.
English Language Abstract for JP 04/230312.
English Language Abstract for JP 10/251118.
English Language Abstract for JP 10/120903.
Notice of Allowance in co-pending U.S. Appl. No. 10/746,612 dated Feb. 23, 2010.
Office Action in co-pending U.S. Appl. No. 09/733,897 dated Feb. 17, 2010.
Office Action in co-pending U.S. Appl. No. 09/733,900 dated Jan. 21, 2010.
Office Action in co-pending U.S. Appl. No. 10/494,864 dated Dec. 29, 2009.
Office Action in co-pending U.S. Appl. No. 10/699,780 dated Feb. 3, 2010.
Office Action in co-pending U.S. Appl. No. 10/747,412 dated Jan. 20, 2010.
Office Action in co-pending U.S. Appl. No. 11/312,338 dated Mar. 4, 2010.
McCutcheon's vol. 1: Emulsifiers & Detergents, North American Edition, M.C. Publishing Co., Glen Rock Nj (1993), pp. 272-273.
Co-Pending U.S. Appl. No. 10/918,579, Title: Compositions Containing Heteropolymers and Oilsoluble Esters and Methods of Using Same filed Aug. 16, 2004.
Co-Pending U.S. Appl. No. 10/933,430, Title: Cosmetic Composition Comprising a Polymer Blend filed Nov. 22, 2004.
Co-Pending U.S. Appl. No. 10/933,431, Title: A Transfer-Free Composition Structured in Rigid Form by a Polymer filed Nov. 22, 2004.
Co-Pending U.S. Appl. No. 10/990,475, Title: Use of a Polymer for Obtaining an Express Make-Up of Keratin Materials filed Nov. 18, 2004.
Co-Pending Application No. Not Yet Assigned, Title: Cosmetic Composition Comprising Two Different Hetero Polymers and Method of Using Same U.S. Filing Date: Dec. 23, 2004.
Co-Pending U.S. Appl. No. 09/618,066; Title: Compositions in Rigid Form Structured With a Polymer Inventors: Véronique Ferrari and Pascal Simon filed Jul. 17, 2000.

Co-Pending U.S. Appl. No. 09/685,577; Title: Compositions in Rigid Form Structured With a Polymer Inventors: Véronique Ferrari and Pascal Simon filed Oct. 11, 2000.
Co-Pending U.S. Appl. No. 09/685,578; Title: Composition Containing a Liquid Fatty Phase Gelled With a Polyamide Containing Ester End Groups Inventor: Véronique Ferrari U.S. Filing Date: CIP filed Oct. 11, 2000.
Co-Pending U.S. Appl. No. 09/733,896; Title: Compositions Containing Heteropolymers and Oil-Soluble Polymers and Methods of Using Same Inventors: Carlos Pinzon and Paul Thau filed Dec. 12, 2000.
Co-Pending U.S. Appl. No. 09/733,897; Title: Compositions Containing Heteropolymers and Methods of Using Same Inventors: Carlos Pinzon and Paul Thau filed Dec. 12, 2000.
Co-Pending U.S. Appl. No. 09/733,898; Title: Compositions Containing Heteropolymers and Oil-Soluble Esters and Methods of Using Same Inventors: Carlos Pinzon and Paul Thau filed Dec. 12, 2000.
Co-Pending U.S. Appl. No. 09/733,900; Title: Cosmetic Compositions Containing Heteropolymers and Oil-Soluble Cationic Surfactants and Methods of Using Inventors: Carlos Pinzon and Paul Thau filed Dec. 12, 2000.
Co-Pending U.S. Appl. No. 10/182,830; Title: Cosmetic Composition Comprising Hetero Polymers and a Solid Substance and Method of Using Same filed Aug. 2, 2002.
Co-Pending U.S. Appl. No. 10/203,018; Title: Composition Comprising At Least One Hetero Polymer and At Least One Inert Filler and Methods for Use filed Aug. 5, 2002.
Co-Pending U.S. Appl. No. 10/203,254; Title: Cosmetic Compositions Containing At Least One Heteropolymer and At Least One Gelling Agent and Methods of Using the Same filed Aug. 7, 2002.
Co-Pending U.S. Appl. No. 10/413,217, Title: Methods of Dispersing At Least One Coloring Agent Using At Least One Heteropolymer filed Apr. 15, 2003.
Co-Pending U.S. Appl. No. 10/450,108, Title: Cosmetic Composition Comprising a Polymer and Fibres filed Jun. 11, 2003.
Co-Pending U.S. Appl. No. 10/459,636, Title: Cosmetic Emulsions Containing At Least One Hetero Polymer and At Least One Sunscreen and Methods of Using the Same filed Jun. 12, 2003.
Co-Pending U.S. Appl. No. 10/466,166, Title: Cosmetic Composition Comprising a Mixture of Polymers filed Jul. 14, 2003.
Co-Pending U.S. Appl. No. 10/618,315, Title: Cosmetic Compositions Comprising a Structuring Agent, Silicone Powder and Swelling Agent filed Jul. 11, 2003.
Co-Pending U.S. Appl. No. 10/699,780, Title: Methods of Dispersing At Least One Coloring Agent Using At Least One Heteropolymer filed Nov. 4, 2003.
Co-Pending U.S. Appl. No. 10/746,612, Title: Cosmetic Compositions Comprising a Structuring Agent, Silicone Powder and Swelling Agent filed Dec. 22, 2003.
Co-Pending U.S. Appl. No. 10/747,412, Title: Cosmetic Emulsions Containing at Least One Hetero Polymer and at Least One Sunscreen and Methods of Using the Same filed Dec. 22, 2003.
Co-Pending U.S. Appl. No. 10/787,440, Title: Composition Comprising at Least One Hetero Polymer and at Least One Inert Filler and Methods for Use filed Feb. 27, 2004.
Co-Pending U.S. Appl. No. 10/787,441, Title: Cosmetic Composition Comprising Hetero Polymers and a Solid Substance and Methods of Using Same filed Feb. 27, 2004.
French Search Report in FR 0016164, dated Sep. 6, 2001.
French Search Report in FR 0016180, dated Oct. 16, 2001.
French Search Report in FR 0100479, dated Sep. 17, 2001.
French Search Report in FR 0100620, dated Nov. 6, 2001.
French Search Report in FR 0100623, dated Oct. 9, 2001.
French Search Report in FR 0114529, dated Aug. 26, 2002.
French Search Report in FR 0114530, dated Aug. 26, 2002.
French Search Report in FR 9909176, dated Mar. 23, 2000.
French Search Report in FR 9909177, dated Mar. 30, 2000.
French Search Report in FR 9916588, dated Oct. 16, 2000.
International Search Report in PCT/FR01/00229, dated Apr. 18, 2001.
International Search Report in PCT/FR01/01958, dated Oct. 26, 2001.
International Search Report in PCT/FR01/03937, dated Apr. 23, 2002.
International Search Report in PCT/FR01/03938, dated Jun. 10, 2002.
International Search Report in PCT/FR01/03939 (priority document for FR 0016164), dated Apr. 15, 2002.
International Search Report in PCT/FR01/03940 (priority document for FR 0016161), dated Mar. 13, 2002.
International Search Report in PCT/FR01/03945 (priority document for FR 0016163), dated May 31, 2002.
International Search Report in PCT/FR02/00129, dated Jun. 14, 2002.
International Search Report in PCT/FR02/00144 (priority document for FR 0100479), dated Jun. 14, 2002.
International Search Report in PCT/FR02/00194, dated Jun. 12, 2002.
International Search Report in PCT/IB00/02000, dated Aug. 8, 2001.
International Search Report in PCT/IB00/02002, dated Sep. 4, 2001.
International Search Report in PCT/IB00/02006, dated Aug. 8, 2001.
International Search Report in PCT/IB01/02780, dated Apr. 10, 2002.
International Search Report in PCT/IB01/02786, dated Oct. 2, 2002.
International Search Report in PCT/IB01/02820, dated May 27, 2002.
International Search Report in PCT/IB01/02833, dated May 24, 2002.
International Search Report in PCT/IB01/02840, dated Jun. 11, 2002.
International Search Report in PCT/US 00/33596, dated Aug. 8, 2001.
International Search Report in PCT/US 01/47459, dated Feb. 6, 2003.
International Search Report in PCT/US 01/47496, dated Feb. 26, 2003.
International Search Report in PCT/US 01/47497, dated Dec. 2, 2002.
Office Action in co-pending U.S. Appl. No. 09/733,900 dated Dec. 1, 2004.
Office Action in co-pending U.S. Appl. No. 09/618,066 dated Dec. 21, 2001.
Office Action in co-pending U.S. Appl. No. 09/618,066 dated Jul. 15, 2002.
Office Action in co-pending U.S. Appl. No. 09/618,066 dated Jul. 16, 2003.
Office Action in co-pending U.S. Appl. No. 09/618,066 dated Nov. 19, 2003.
Office Action in co-pending U.S. Appl. No. 09/685,577 dated Aug. 11, 2004.
Office Action in co-pending U.S. Appl. No. 09/685,577 dated Jul. 15, 2002.
Office Action in co-pending U.S. Appl. No. 09/685,577 dated Jul. 16, 2003.
Office Action in co-pending U.S. Appl. No. 09/685,577 dated Nov. 19, 2003.
Office Action in co-pending U.S. Appl. No. 09/685,578 dated Aug. 11, 2004.
Office Action in co-pending U.S. Appl. No. 09/685,578 dated May 7, 2003.
Office Action in co-pending U.S. Appl. No. 09/685,578 dated Nov. 19, 2003.
Office Action in co-pending U.S. Appl. No. 09/733,896 dated Jan. 28, 2003.
Office Action in co-pending U.S. Appl. No. 09/733,896 dated Jul. 19, 2002.
Office Action in co-pending U.S. Appl. No. 09/733,896 dated Nov. 18, 2003.
Office Action in co-pending U.S. Appl. No. 09/733,897 dated Apr. 15, 2002.
Office Action in co-pending U.S. Appl. No. 09/733,897 dated Apr. 23, 2003.
Office Action in co-pending U.S. Appl. No. 09/733,897 dated Aug. 29, 2002.
Office Action in co-pending U.S. Appl. No. 09/733,897 dated May 6, 2004.

Office Action in co-pending U.S. Appl. No. 09/733,898 dated Apr. 29, 2003.
Office Action in co-pending U.S. Appl. No. 09/733,898 dated Aug. 28, 2002.
Office Action in co-pending U.S. Appl. No. 09/733,898 dated Dec. 23, 2003.
Office Action in co-pending U.S. Appl. No. 09/733,900 dated Apr. 7, 2004.
Office Action in co-pending U.S. Appl. No. 09/733,900 dated Jul. 16, 2003.
Office Action in co-pending U.S. Appl. No. 09/749,036 dated Aug. 13, 2003.
Office Action in co-pending U.S. Appl. No. 09/749,036 dated Jul. 16, 2002.
Office Action in co-pending U.S. Appl. No. 09/749,036 dated May 5, 2004.
Office Action in co-pending U.S. Appl. No. 09/899,909 dated Dec. 18, 2001.
Office Action in co-pending U.S. Appl. No. 09/937,314 dated May 19, 2004.
Office Action in co-pending U.S. Appl. No. 09/971,028 dated Aug. 11, 2003.
Office Action in co-pending U.S. Appl. No. 09/971,028 dated Mar. 26, 2003.
Office Action in co-pending U.S. Appl. No. 10/012,029 dated Nov. 20, 2002.
Office Action in co-pending U.S. Appl. No. 10/012,029 dated Sep. 8, 2003.
Office Action in co-pending U.S. Appl. No. 10/012,051 dated Jan. 14, 2003.
Office Action in co-pending U.S. Appl. No. 10/012,051 dated May 14, 2004.
Office Action in co-pending U.S. Appl. No. 10/012,051 dated Oct. 3, 2003.
Office Action in co-pending U.S. Appl. No. 10/012,052 dated Nov. 6, 2003.
Office Action in co-pending U.S. Appl. No. 10/012,052 dated Aug. 9, 2004.
Office Action in co-pending U.S. Appl. No. 10/046,568 dated Dec. 30, 2003.
Office Action in co-pending U.S. Appl. No. 10/046,568 dated Jun. 12, 2003.
Office Action in co-pending U.S. Appl. No. 10/046,568 dated Nov. 5, 2002.
Office Action in co-pending U.S. Appl. No. 10/046,568 dated Sep. 22, 2004.
Office Action in co-pending U.S. Appl. No. 10/047,987 dated Dec. 11, 2003.
Office Action in co-pending U.S. Appl. No. 10/047,987 dated Sep. 7, 2004.
Office Action in co-pending U.S. Appl. No. 10/182,830 dated Aug. 24, 2004.
Office Action in co-pending U.S. Appl. No. 10/198,931 dated Dec. 18, 2003.
Office Action in co-pending U.S. Appl. No. 10/198,931 dated Sep. 1, 2004.
Office Action in co-pending U.S. Appl. No. 10/203,018 dated May 19, 2004.
Office Action in co-pending U.S. Appl. No. 10/312,083 dated Oct. 1, 2004.
Office Action in co-pending U.S. Appl. No. 10/413,217 dated Sep. 9, 2004.
Office Action in co-pending U.S. Appl. No. 10/699,780 dated Sep. 22, 2004.
Office Action in co-pending U.S. Appl. No. 10/746,612 dated Sep. 20, 2004.
Office Action in co-pending U.S. Appl. No. 10/787,440 dated Aug. 24, 2004.
Origins Full Story™ Lush lash mascara product packaging, believed to have first been sold in 2003.
P. Terech, "Low-Molecular Weight Organogelators," in Specialist Surfactants, ch. 8, pp. 208-268 (I.D. Robb, ed., 1997).
PCT Application No. PCT/IB00/02000; Title: Composition Comprising At Least One Hetero Polymer and At Least One Inert Filler and Methods for Use Inventors: Véronique Ferrari et al. International Filing Date: Dec. 12, 2000.
PCT Application No. PCT/IB00/02006; Title: Cosmetic Compositions Containing At Least One Heteropolymer and At Least One Gelling Agent and Methods of Using the Same Inventor: Véronique Ferrari International Filing Date:Dec. 12, 2000.
PCT Application No. PCT/US00/33596; Title Cosmetic Composition Comprising Hetero Polymers and a Solid Substance and Method of Using Same Inventors: Roberto Cavazzuti et al. International Filing Date: Dec. 12, 2000.
U.S. District Court for the District of New Jersey Civil Docket for L'Oreal S.A., et al. v. Estee Lauder Companies, Inc., et al. Civ. No. 04-1660 (HAA) (D.N.J. filed Apr. 4, 2004) (retrieved Jan. 2, 2005).
Co-Pending U.S. Appl. No. 09/685,578; Title: Compositions Containing a Fatty Phase Gelled With a Polyamide Containing Ester End Groups Inventors: Véronique Ferrari filed Jul. 17, 2000.
Co-Pending U.S. Appl. No. 09/685,578; Title: Compositions Containing a Fatty Phase Gelled With a Polyamide Containing Ester End Groups Inventors: Véronique Ferrari U.S. Filing Date: CIP filed Oct. 11, 2000.
PCT Application No. PCT/US00/33596; Title: Cosmetic Composition Comprising Hetero Polymers and a Solid Substance and Method of Using Same Inventor: Robert Cavazzuti et al. International Filing Date: Dec. 12, 2000.
Co-Pending U.S. Appl. No. 09/733,896; Title: Compositions Containing Heteropolymers and Oil-Soluble Esters and Methods of U sing Same Inventors: Carlos Pinzon and Paul Thau filed Dec. 12, 2000.
Co-Pending U.S. Appl. No. 09/733,898; Title: Compositions Containing Heteropolymers and Oil-Soluble Esters and Methods of Using Same Inventors: Carlos Pinzon and Paul Thau filed Dec. 12, 2000.
Co-Pending U.S. Appl. No. 09/733,897; Title: Compositions Containing Heteropolymers and Methods of Using Same Inventors: Carlos Pinzon and Paul Thau filed Dec. 12, 2000 Amendment filed Jan. 4, 2002 (adding claims 41-102).
PCT Application No. PCT/IB00/02000; Title: Compositions Comprising At Least One Heteropolymer and At Least One Inert Filler and Methods for Use Inventor: Carlos Pinzon and Paul Thau International Filing Date: Dec. 12, 2000.
PCT Application No. PCT/IB00/02006; Title: Cosmetic Compositions Containing At Least One Heteropolymer and At Least One Gelling Agent and Methods of Using the Same Inventors: Carlos Pinzon and Paul Thau International Filing Date: Dec. 12, 2000.
Bangham, A.D. et al. Diffusion of Univalent Ions across the Lamellae of Swollen Phospholipids, Journal of Molecular Biology, pp. 238-252, vol. 13, Aug. to Oct. 1965.
Co-Pending U.S. Appl. No. 11/826,997; Title: Composition Structured With a Polymer Containing a Heteroatom and an Organogelator; filed Jul. 19, 2007.
Co-Pending U.S. Appl. No. 09/733,899; Title: Cosmetic Compositions Containing At Least One Hetero Polymer and At Least One Film-Forming Silicone Resin and Methods of Using Inventors: Mohamed Kanji et al., filed Dec. 12, 2000.
Co-Pending U.S. Appl. No. 10/618,315; Title: Cosmetic Compositions Comprising a Structuring Agent, Silicone Powder and Swelling Agent filed Jul. 11, 2003.
Co-Pending U.S. Appl. No. 10/990,475, Title: Use of a Polymer for Obtaining an Express Make-Up of Keratin Materials, filed Nov. 18, 2004.
Co-Pending U.S. Appl. No. 10/993,430, Title: Cosmetic Composition Comprising a Polymer Blend filed Nov. 22, 2004.
Co-Pending U.S. Appl. No. 10/993,431, Title: A Transfer-Free Composition Structured in Rigid Form by a Polymer, filed Nov. 22, 2004.
Co-Pending U.S. Appl. No. 11/019,382, Title: Cosmetic Composition Comprising Two Different Hetero Polymers and Method of Using Same, filed Dec. 23, 2004.
Co-Pending U.S. Appl. No. 11/212,811, Title: A Transfer-Free Mascara Composition Comprising At Least One Volatile Solvent and At Least One Polymer, filed Aug. 29, 2005.

Co-Pending U.S. Appl. No. 11/312.338, Title: Composition and Process for Coating Keratin Fibers, filed Dec. 21, 2005.
English language Derwent abstract for JP 64-90110.
English language Derwent Abstract for JP 7-258460.
English language esp@cenet Abstract of JP 7 089826.
English language Derwent abstract of WO 93/04665.
English language Derwent Abstract for WO 96/38126.
English language esp@cenet Abstract for WO 98/25922.
Harry's Cosmeticology 375-383 (J.B. Wilkinson & R.J. Moore eds., Chemical Pub. 7th ed. 1982).
International Search Report in PCT/US03/41618, dated Mar. 11, 2005.
International Search Report in PCT/US04/01071, dated Feb. 25, 2005.
Irving R. Schmolka. PhD., "Gel Cosmetics," Cosmetics & Toletries, vol. 99, pp. 69-76, Nov. 1984.
Milan Jokic et al., A Novel Type of Small Organic Gelators: Bis(Amino Acid) Oxalyl Amides, 1995 J. Chem. Soc., Chem. Commun., 1723-1724.
Office Action in co-pending U.S. Appl. No. 09/685,578 dated Feb. 8, 2005.
Office Action in co-pending U.S. Appl. No. 09/733,896 dated Jan. 30, 2006.
Office Action in co-pending U.S. Appl. No. 09/733,897 dated Jul. 27, 2006.
Office Action in co-pending U.S. Appl. No. 09/733,897 dated Jan. 18, 2007.
Office Action in co-pending U.S. Appl. No. 09/733,898 dated Jan. 11, 2006.
Office Action in co-pending U.S. Appl. No. 09/749,036 dated Aug. 24, 2007.
Office Action in co-pending U.S. Appl. No. 09/749,036 dated Jan. 17, 2007.
Office Action in co-pending U.S. Appl. No. 09/749,036 dated Nov. 23, 2005.
Office Action in co-pending U.S. Appl. No. 09/749,036 dated Aug. 24, 2007).
Office Action in co-pending U.S. Appl. No. 10/129,377 dated Jan. 13, 2006.
Office Action in co-pending U.S. Appl. No. 10/129,377 dated Oct. 10, 2006.
Office Action in co-pending U.S. Appl. No. 10/129,377 dated Jul. 13, 2007.
Office Action in co-pending U.S. Appl. No. 10/182,830 dated Apr. 4, 2005.
Office Action in co-pending U.S. Appl. No. 10/182,830 dated Nov. 25, 2005.
Office Action in co-pending U.S. Appl. No. 10/182,830, dated May 17, 2006.
Office Action in co-pending U.S. Appl. No. 10/203,254 dated Dec. 5, 2005.
Office Action in co-pending U.S. Appl. No. 10/203,254 dated Jun. 1, 2006.
Office Action in co-pending U.S. Appl. No. 10/312,083 dated Sep. 28, 2005.
Office Action in co-pending U.S. Appl. No. 10/312,083 dated Apr. 6, 2006.
Office Action in co-pending U.S. Appl. No. 10/312,083 dated Sep. 25, 2006.
Office Action in co-pending U.S. Appl. No. 10/450,108 dated Mar. 21, 2007.
Office Action in co-pending U.S. Appl. No. 10/459,636, dated Aug. 31, 2006.
Office Action in co-pending U.S. Appl. No. 10/466,166 dated Jun. 25, 2007.
Office Action in co-pending U.S. Appl. No. 10/699,780 dated Oct. 9, 2007.
Office Action in co-pending U.S. Appl. No. 10/699,780, dated Sep. 25, 2006.
Office Action in co-pending U.S. Appl. No. 10/746,612 dated Feb. 17, 2006.
Office Action in co-pending U.S. Appl. No. 10/746,612 dated Nov. 3, 2006.
Office Action in co-pending U.S. Appl. No. 10/787,441, dated Apr. 5, 2005.
Office Action in co-pending U.S. Appl. No. 10/990,475 dated Jan. 23, 2007.
Office Action in co-pending U.S. Appl. No. 10/990,475 dated May 1, 2006.
Office Action in co-pending U.S. Appl. No. 10/990,475 dated Nov. 2, 2005.
Office Action in co-pending U.S. Appl. No. 10/993,431 dated Oct. 18, 2007.
Office Action in co-pending U.S. Appl. No. 11/212,811 dated May 17, 2007.
Office Action in co-pending U.S. Appl. No. 11/212,811 dated Aug. 24, 2006.
Office Action in co-pending U.S. Appl. No. 11/212,811 dated Nov. 17, 2005.
Richard H. Lewis, Sr., "Fatty Acid," Hawley's Condensed Chemical Dictionary 487 (13th ed., 1997).
Richard M. Sayre, "Physical Sunscreens," J. Soc. Cosmes. Chem., 41, 103-109 (Mar./Apr. 1990).
Toshimi Shimizu et al., Stereochemical Effect of Even-Odd Connecting Links on Supramolecular Assemblies Made of 1-Glucosamide Bolaamphiphiles, J. Am Chem. Soc. 1997, 119, 2812-2818.
Co-Pending U.S. Appl. No. 10/182,830; Title: Cosmetic Composition Comprising Hetero Polymers and a Solid Substance and Method of Using Same filed Aug. 2, 2002.
Co-Pending U.S. Appl. No. 10/203,018; Title: Composition Comprising At Least One Hetero Polymer and At Least One Inert Filler and Methods for Use filed Aug. 5, 2002.
Co-Pending U.S. Appl. No. 10/203,254; Title: Cosmetic Compositions Containing At Least One Heteropolymer and At Least One Gelling Agent and Methods of Using the Same filed Aug. 7, 2002.
Co-Pending U.S. Appl. No. 10/413,217, Title: Methods of Dispersing At Least One Coloring Agent Using At Least One Heteropolymer filed Apr. 15, 2003.
Co-Pending U.S. Appl. No. 10/450,108, Title: Cosmetic Composition Comprising a Polymer and Fibres filed Jun. 11, 2003.
Co-Pending U.S. Appl. No. 10/459,636, Title: Cosmetic Emulsions Containing At Least One Hetero Polymer and At Least One Sunscreen and Methods of Using the Same filed Jun. 12, 2003.
Co-Pending U.S. Appl. No. 10/466,166, Title: Cosmetic Composition Comprising a Mixture of Polymers filed Jul. 14, 2003.
Co-Pending U.S. Appl. No. 10/618,315, Title: Cosmetic Compositions Comprising a Structuring Agent, Silicone Powder and Swelling Agent filed Jul. 11, 2003.
Co-Pending U.S. Appl. No. 10/699,780, Title: Methods of Dispersing At Least One Coloring Agent Using At Least One Heteropolymer filed Nov. 4, 2003.
Co-Pending U.S. Appl. No. 10/746,612, Title: Cosmetic Compositions Comprising a Structuring Agent, Silicone Powder and Swelling Agent filed Dec. 22, 2003.
Co-Pending U.S. Appl. No. 10/747,412, Title: Cosmetic Emulsions Containing At Least One Hetero Polymer and At Least One Sunscreen and Methods of Using the Same filed Dec. 22, 2003.
Co-Pending U.S. Appl. No. 10/787,440, Title: Compostition Comprising At Least One Hetero Polymer and At Least One Inert Filler and Methods for Use filed Feb. 27, 2004.
Co-Pending U.S. Appl. No. 10/787,441, Title: Cosmetic Composition Comprising Hetero Polymers and a Solid Substance and Method of Using Same filed Feb. 27, 2004.
English language abstract of JP 53/043577 from Patent Abstracts of Japan.
English language abstract of JP 56/123909 from Patent Abstracts of Japan.
English language abstract of JP 56/166276 from Patent Abstracts of Japan.
English language Derwent abstract of JP 78/043577.
English language Derwent abstract of DE 195 43 988 A1.
English language Derwent abstract of DE 197 07 309 A1.
English language Derwent abstract of DE 38 39 136 A.
English language Derwent abstract of EP 0 557 196 A1.
English language Derwent abstract of EP 0 609 132 B1.
English language Derwent abstract of EP 0 749 746 A1.

English language Derwent abstract of EP 0 749 747 A1.
English language Derwent abstract of EP 0 775 483 A1.
English language Derwent abstract of EP 0 847 752 A1.
English language Derwent abstract of EP 0 879 592 A2.
English language Derwent abstract of EP 0 887 073 A1.
English language Derwent abstract of EP 0 930 058 B1.

English language Derwent abstract of EP 0 930 060 A1.
English language Derwent abstract of EP 0 958 811 A1.
English language Derwent abstract of EP 0 959 066 A2.
English language Derwent abstract of EP 0 959 091 A1.

* cited by examiner

COSMETIC COMPOSITIONS CONTAINING AT LEAST ONE HETERO POLYMER AND AT LEAST ONE FILM-FORMING SILICONE RESIN AND METHODS OF USING

The present invention relates to a composition, in one embodiment a transfer resistant cosmetic composition, which may also be at least one of pliable and comfortable to wear upon application to a substrate. The composition comprises, more particularly, at least one structuring polymer and at least one silicone resin. The invention, in one embodiment, relates to cosmetic, dermatological, and pharmaceutical products containing this composition. As used herein, the expression "at least one" means one or more and thus includes individual components as well as mixtures/combinations.

Many cosmetic compositions, including pigmented cosmetics such as foundations, concealers, lipsticks, mascaras, and other cosmetic and sunscreen compositions, have been developed for longer wear and non-transfer properties. This is accomplished by the use of compositions that form a film after application. Such compositions generally contain volatile solvents which evaporate on contact with the skin or other keratinous tissue, leaving behind a layer comprising waxes and/or resins, pigments, fillers, and actives. However, these compositions tend to be uncomfortable for the wearer as the composition remains on the skin or other keratinous tissue as a brittle or non-flexible film. Such compositions may not be either pliable or soft, and they may not be comfortable to wear. There may also be a tendency for such compositions to flake off because of poor adherence to the skin or other keratinous tissue. Furthermore, compositions may have a tendency to be tacky, resulting in poor application and spreadability characteristics.

The need therefore still remains for improved long-wearing cosmetic compositions which transfer little or not at all, i.e., "transfer-free" or transfer resistant compositions which also possess good cosmetic properties such as pliability and comfort. For example, a composition which is transfer resistant may deposit a film onto a keratinous substance which may not transfer when the keratinous substance comes into contact with, for example, skin, a cup, paper, cigarette, or a handkerchief.

To achieve at least one of these and other advantages, the present invention, in one aspect, provides a composition comprising at least one structuring polymer comprising a polymer skeleton which comprises at least one hydrocarbon-based repeating unit comprising at least one hetero atom. The composition also comprises at least one film-forming silicone resin. The present invention also relates to a method for making such a composition.

It is to be understood that both the foregoing general description and the following detailed description are exemplary and explanatory only, and are not restrictive of the invention.

The invention, in one aspect, provides compositions comprising at least one structuring polymer and at least one film-forming silicone resin. In one embodiment, the at least one structuring polymer and the at least one film-forming silicone resin are present in an amount effective to provide transfer resistant properties, and may also provide at least one of the following properties: pliability, softness, and wearing comfort.

One subject of the invention is cosmetic and/or dermatological compositions which are useful for the care, make-up and/or treating of at least one keratinous material which may be of suitable hardness to allow preparation of these compositions in the form of a stick or other structured form which may be stable.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as bending or leaning if the composition is in stick form, phase separation, melting, or syneresis. As used herein syneresis is the appearance of droplets on the surface of a composition that are visible to the naked eye. The stability is further tested by repeating the 8 week test at 4° C., 37° C., 45° C., 50° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

Structured liquid fatty phases in cosmetic or dermatological products are known in the art. As used herein, "structured" means gelled and/or rigidified. Structured liquid fatty phases may be found in solid compositions such as deodorants, balms, lip compositions, concealer products and cast foundations.

The compositions of the invention, in one embodiment, may comprise at least one liquid fatty phase. As used herein, "liquid fatty phase" means a fatty phase which is liquid at room temperature (25° C.) and at atmospheric pressure (760 mmHg) and which is composed of at least one fatty substance, such as an oil, which is liquid at room temperature and not soluble in water. If the at least one liquid fatty phase comprises two or more fatty substances, they should be mutually compatible.

Structured liquid fatty phases may make it possible to control the exudation of the liquid fatty phase from the solid compositions of which they are components including exudation in a wet or hot atmosphere or environment. Structuring of the liquid fatty phase may also limit bleeding of this phase outside of the intended area of application and especially into wrinkles and fine lines after it has been deposited, for example, on keratinous material. As used herein, "keratinous material" is meant to comprise hair, lips, skin, scalp and superficial body growths such as eyelashes, eyebrows and nails.

The invention applies not only to make-up products for at least one keratinous material such as lip compositions, lip pencils, foundations including foundations which may be cast in the form of a stick or a dish, concealer products, temporary tattoo products, eyeliners, mascara bars but also to body hygiene products such as deodorant sticks, and to care products and products for treating at least one keratinous material such as sunscreen and after-sun products which may be in stick form. The present invention may be in the form of mascara product including mascara bars, an eyeliner product, a foundation product, a lipstick product, a blush for cheeks or eyelids, a deodorant product, a make-up product for the body, a make-up-removing product, an eyeshadow product, a face powder product, a concealer product, a treating shampoo product, a hair conditioning product, a sun screen, colorant for the skin or hair, or skin care formula such as, for example, anti-pimple or shaving cut formulas. As defined herein, a deodorant product is a body hygiene product and does not relate to care, make-up, or treatment of keratin materials, including keratin fibers, skin, or lips.

For example, the composition of the present invention may be in a form chosen from a paste, a solid, a gel, and a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel, including anhydrous gels. In one embodiment, the composition of the invention is anhydrous. The composition of the invention may, for example, comprise an external or continuous fatty phase. In another embodiment, the composition of the invention is transparent or clear, including for example, a composition without pigments. The composition can also be in a form chosen from a translucent anhydrous gel and a transparent anhydrous gel. The composition can also be a molded composition or cast as a stick or a dish. The composition in one embodiment is a solid such as a molded stick or a poured stick.

Structuring Polymer

In one embodiment, the at least one structuring polymer in the composition of the invention is a solid that is not deformable at room temperature (25° C.) and atmospheric pressure (760 mmHg). In a further embodiment, the at least one structuring polymer is capable of structuring the composition without opacifying it. As defined above, the at least one structuring polymer of the present invention comprises a polymer skeleton comprising at least one hydrocarbon-based repeating unit comprising at least one hetero atom. In one embodiment, the at least one structuring polymer further comprises at least one terminal fatty chain chosen from alkyl and alkenyl chains, such as of at least 4 atoms, and further such as comprising 8 to 120 carbon atoms, bonded to the polymer skeleton via at least one linking group. The terminal fatty chain may, for example, be functionalized. The at least one structuring polymer may also further comprise at least one pendant fatty chain chosen from alkyl and alkenyl chains, such as of at least 4 atoms, and further such as comprising 8 to 120 carbon atoms, bonded to any carbon or hetero atom of the polymer skeleton via at least one linking group. The pendant fatty chain may, for example, be functionalized. The at least one structuring polymer may comprise both at least one pendant fatty chain and at least one terminal fatty chain as defined above, and one or both types of chains can be functionalized.

In one embodiment, the structuring polymer comprises at least two hydrocarbon-based repeating units. As a further example, the structuring polymer comprises at least three hydrocarbon-based repeating units and as an even further example, the at least three repeating units are identical.

As used herein, "functionalized" means comprising at least one functional group. Non-limiting examples of functional groups include hydroxyl groups, ether groups, oxyalkylene groups, polyoxyalkylene groups, carboxylic acid groups, amine groups, amide groups, halogen containing groups, including fluoro and perfluoro groups, halogen atoms, ester groups, siloxane groups and polysiloxane groups.

For purposes of the invention, the expression "functionalized chain" means, for example, an alkyl chain comprising at least one functional (reactive) group chosen, for example, from those recited above. For example, in one embodiment, the hydrogen atoms of at least one alkyl chain may be substituted at least partially with fluorine atoms.

According to the invention, these chains may be linked directly to the polymer skeleton or via an ester function or a perfluoro group.

For the purposes of the invention, the term "polymer" means a compound containing at least 2 repeating units, such as, for example, a compound containing at least 3 repeating units, which may be identical.

As used herein, the expression "hydrocarbon-based repeating unit" includes a repeating unit comprising from 2 to 80 carbon atoms, such as, for example, from 2 to 60 carbon atoms. The at least one hydrocarbon-based repeating unit may also comprise oxygen atoms. The hydrocarbon-based repeating unit may be chosen from saturated and unsaturated hydrocarbon-based repeating units which in turn may be chosen from linear hydrocarbon-based repeating units, branched hydrocarbon-based repeating units and cyclic hydrocarbon-based repeating units. The at least one hydrocarbon-based repeating unit may comprise, for example, at least one hetero atom that is part of the polymer skeleton, i.e., not pendant. The at least one hetero atom may be chosen, for example, from nitrogen, sulphur, and phosphorus. For example, the at least one hetero atom may be a nitrogen atom, such as a non-pendant nitrogen atom. In another embodiment, the at least one hydrocarbon-based repeating unit may comprise at least one hetero atom with the proviso that the at least one hetero atom is not nitrogen. In another embodiment, the at least one hetero atom is combined with at least one atom chosen from oxygen and carbon to form a hetero atom group. In one embodiment, the hetero atom group comprises a carbonyl group.

The at least one repeating unit comprising at least one hetero atom may be chosen, for example, from amide groups, carbamate groups, and urea groups. In one embodiment, the at least one repeating unit comprises amide groups forming a polyamide skeleton. In another embodiment, the at least one repeating unit comprises carbamate groups and/or urea groups forming a polyurethane skeleton, a polyurea skeleton and/or a polyurethane-polyurea skeleton. The pendant chains, for example, can be linked directly to at least one of the hetero atoms of the polymer skeleton. In yet another embodiment, the at least one hydrocarbon-based repeating unit may comprise at least one hetero atom group with the proviso that the at least one hetero atom group is not an amide group. In one embodiment, the polymer skeleton comprises at least one repeating unit chosen from silicone units and oxyalkylene units, the at least one repeating unit being between the hydrocarbon-based repeating units.

In one embodiment, the compositions of the invention comprise at least one structuring polymer with nitrogen atoms, such as amide, urea, or carbamate units, such as amide units, and at least one polar oil.

In one embodiment, in the at least one structuring polymer, the percentage of the total number of fatty chains ranges from 40% to 98% relative to the total number of repeating units and fatty chains, and as a further example, from 50% to 95%. In a further embodiment wherein the polymer skeleton is a polyamide skeleton, in the at least one structuring polymer, the percentage of the total number of fatty chains ranges from 40% to 98% relative to the total number of all amide units and fatty chains, and as a further example, from 50% to 95%.

In a further embodiment, the nature and proportion of the at least one hydrocarbon-based repeating unit comprising at least one hetero atom depends on the nature of a liquid fatty phase of the composition and is, for example, similar to the nature of the fatty phase. For example, not to be limited as to theory, the more polar the hydrocarbon-based repeating units containing a hetero atom, and in high proportion, which corresponds to the presence of several hetero atoms, the greater the affinity of the at least one structuring polymer to polar oils. Conversely, the more non-polar, or even apolar, and lesser in proportion the hydrocarbon-based repeating units containing a hetero atom, the greater the affinity of the polymer for apolar oils.

In another embodiment, the invention is drawn to a structured composition containing at least one liquid fatty phase structured with at least one structuring polymer, wherein the at least one structuring polymer is a polyamide comprising a polymer skeleton comprising at least one amide repeating unit and optionally at least one pendant fatty chain and/or at least one terminal chain that are optionally functionalized and comprise from 8 to 120 carbon atoms, bonded to at least one of the amide repeating units via at least one linking group. The liquid fatty phase further contains at least one organogellator for gelling the liquid fatty phase. The at least one liquid fatty phase, the at least one structuring polyamide and the at least one organogellator together form a physiologically acceptable medium.

When the structuring polymer has amide repeating units, the pendant fatty chains may be linked to at least one of the nitrogen atoms in the amide repeating units.

The structuring polymer, for example the polyamide polymer, may have a weight-average molecular mass of less than 100,000, such as less than 50,000. In another embodiment, the weight-average molecular mass may range from 1000 to 30,000, such as from 2000 to 20,000, further such as from 2000 to 10,000.

As discussed, the at least one structuring polymer may, for example, be chosen from polyamide polymers. A polyamide polymer may comprise, for example, a polymer skeleton which comprises at least one amide repeating unit, i.e., a polyamide skeleton. In one embodiment, the polyamide skeleton may further comprise at least one terminal fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group, and/or at least one pendant fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group. In one embodiment, the polyamide skeleton may comprise at least one terminal fatty chain chosen from fatty chains comprising 8 to 120 carbon atoms, such as, for example, 12 to 68 carbon atoms, bonded to the at least one polyamide skeleton via at least one linking group and/or at least one pendant fatty chain chosen from fatty chains comprising 8 to 120 carbon atoms, such as, for example, 12 to 68 carbon atoms, bonded to the at least one polyamide skeleton via at least one linking group, such as bonded to any carbon or nitrogen of the polyamide skeleton via the at least one linking group. In one embodiment, the at least one linking group is chosen from single bonds and urea, urethane, thiourea, thiourethane, thioether, thioester, ester, ether and amine groups. For example, the at least one linking group is chosen from ureas, esters, and amines, and as a further example, is chosen from esters and amines. The bond is, for example, an ester bond. In one embodiment, these polymers comprise a fatty chain at each end of the polymer skeleton, such as the polyamide skeleton.

In one embodiment, due to the presence of at least one chain, the polyamide polymers may be readily soluble in oils (i.e., water-immiscible liquid compounds) and thus may give macroscopically homogeneous compositions even with a high content (at least 25%) of the polyamide polymers, unlike certain polymers of the prior art that do not contain such alkyl or alkenyl chains at the end of the polyamide skeleton. As defined herein, a composition is soluble if it has a solubility of greater than 0.01 g per 100 ml of solution at 25° C.

In a further embodiment, the polyamide polymers can be chosen from polymers resulting from at least one polycondensation reaction between at least one acid chosen from dicarboxylic acids comprising at least 32 carbon atoms, such as 32 to 44 carbon atoms, and at least one amine chosen from diamines comprising at least 2 carbon atoms, such as from 2 to 36 carbon atoms, and triamines comprising at least 2 carbon atoms, such as from 2 to 36 carbon atoms. The dicarboxylic acids can, for example, be chosen from dimers of at least one fatty acid comprising at least 16 carbon atoms, such as oleic acid, linoleic acid and linolenic acid. The at least one amine can, for example, be chosen from diamines, such as ethylenediamine, hexylenediamine, hexamethylenediamine, phenylenediamine and triamines, such as ethylenetriamine.

The polyamide polymers may also be chosen from polymers comprising at least one terminal carboxylic acid group. The at least one terminal carboxylic acid group can, for example, be esterified with at least one alcohol chosen from monoalcohols comprising at least 4 carbon atoms. For example, the at least one alcohol can be chosen from monoalcohols comprising from 10 to 36 carbon atoms. In a further embodiment, the monoalcohols can comprise from 12 to 24 carbon atoms, such as from 16 to 24 carbon atoms, and for example 18 carbon atoms.

In one embodiment, the at least one polyamide polymer may be chosen from those described in U.S. Pat. No. 5,783,657, the disclosure of which is incorporated herein by reference, which are polymers of formula (I):

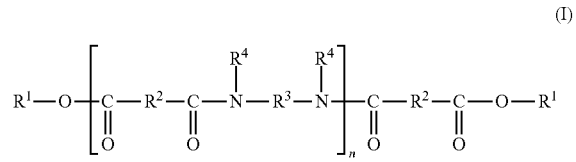

in which:
n is an integer which represents the number of amide units such that the number of ester groups present in said at least one polyamide polymer ranges from 10% to 50% of the total number of all said ester groups and all said amide groups comprised in said at least one polyamide polymer;

$R^1$, which are identical or different, are each chosen from alkyl groups comprising at least 4 carbon atoms and alkenyl groups comprising at least 4 carbon atoms. In one embodiment, the alkyl group comprises from 4 to 24 carbon atoms and the alkenyl group comprises from 4 to 24 carbon atoms;

$R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;

$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and $R^4$, which are identical or different, are each chosen from hydrogen atoms, $C_1$ to $C_{10}$ alkyl groups and a direct bond to at least one group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

In one embodiment, the at least one terminal fatty chain of formula (I) is linked to the last hetero atom, in this case nitrogen, of the polyamide skeleton. In a further embodiment, the terminal chains are functionalized. In another embodiment, the ester groups of formula (I), are linked to the terminal and/or pendant fatty chains, represent from 15% to 40% of the total number of ester and amide groups, such as, for example, from 20% to 35%.

In one embodiment, n may be an integer ranging from 1 to 5, for example, an integer ranging from 3 to 5. In the present invention, $R^1$, which are identical or different, can, for example, each be chosen from $C_{12}$ to $C_{22}$ alkyl groups, such as from $C_{16}$ to $C_{22}$ alkyl groups.

In the present invention, $R^2$, which are identical or different, can, for example, each be chosen from $C_{10}$ to $C_{42}$ alkyl groups. At least 50% of all $R^2$, which are identical or different, can, for example, each be chosen from groups comprising from 30 to 42 carbon atoms. At least 75% of all $R^2$, which are identical or different, can, for example, each be chosen from groups comprising from 30 to 42 carbon atoms. In the two aforementioned embodiments, the remaining $R^2$, which are identical or different, can, for example, each be chosen from $C_4$ to $C_{19}$ groups, such as $C_4$ to $C_{12}$ groups $R^3$, which can be identical or different, can, for example, each be chosen from $C_2$ to $C_{36}$ hydrocarbon-based groups and polyoxyalkylene groups. In another example, $R^3$, which can be identical or different, can each, for example, be chosen from $C_2$ to $C_{12}$ hydrocarbon-based groups. In another embodiment, $R^4$, which can be identical or different, can each be chosen from hydrogen atoms. As used herein, hydrocarbon-based groups may be chosen from linear, cyclic and branched, and saturated and unsaturated groups. The hydrocarbon-based groups can be chosen from aliphatic and aromatic groups. In one example, the hydrocarbon-based groups are chosen from aliphatic groups. The alkyl and alkylene groups may be chosen from linear, cyclic and branched, and saturated and unsaturated groups.

In general, the pendant and terminal fatty chains may be chosen from linear, cyclic and branched, and saturated and unsaturated groups. The pendant and terminal fatty chains can be chosen from aliphatic and aromatic groups. In one example, the pendant and terminal fatty chains are chosen from aliphatic groups.

According to the invention, the structuring of the liquid fatty phase is obtained with the aid of at least one structuring polymer, such as the at least one polymer of formula (I). The at least one polyamide polymer of formula (I) may, for example, be in the form of a mixture of polymers, and this mixture may also comprise a compound of formula (I) wherein n is equal to zero, i.e., a diester.

Non-limiting examples of at least one polyamide polymer which may be used in the composition according to the present invention include the commercial products sold by Arizona Chemical under the names Uniclear 80 and Uniclear 100. These are sold, respectively, in the form of an 80% (in terms of active material) gel in a mineral oil and a 100% (in terms of active material) gel. These polymers have a softening point ranging from 88° C. to 94° C., and may be mixtures of copolymers derived from monomers of (i) $C_{36}$ diacids and (ii) ethylenediamine, and have a weight-average molecular mass of about 6000. Terminal ester groups result from esterification of the remaining acid end groups with at least one alcohol chosen from cetyl alcohol and stearyl alcohol. A mixture of cetyl and stearyl alcohols is sometimes called cetylstearyl alcohol.

Other non-limiting examples of at least one polyamide polymer which may be used in the composition according to the present invention include polyamide polymers resulting from the condensation of at least one aliphatic dicarboxylic acid and at least one diamine, the carbonyl and amine groups being condensed via an amide bond. Examples of these polyamide polymers are those sold under the brand name Versamid by the companies General Mills Inc. and Henkel Corp. (Versamid 930, 744 or 1655) or by the company Olin Mathieson Chemical Corp. under the brand name Onamid, in particular Onamid S or C. These resins have a weight-average molecular mass ranging from 6000 to 9000. For further information regarding these polyamides, reference may be made to U.S. Pat. Nos. 3,645,705 and 3,148,125, the disclosures of which are hereby incorporated by reference.

Other examples of polyamides include those sold by the company Arizona Chemical under the references Uni-Rez (2658, 2931, 2970, 2621, 2613, 2624, 2665, 1554, 2623 and 2662) and the product sold under the reference Macromelt 6212 by the company Henkel. For further information regarding these polyamides, reference may be made to U.S. Pat. No. 5,500,209, the disclosure of which is hereby incorporated by reference. Such polyamides display high melt viscosity characteristics. MACROMELT 6212, for example, has a high melt viscosity at 190° C. of 30-40 poise (as measured by a Brookfield Viscometer, Model RVF #3 spindle, 20 RPM).

In a further embodiment, the at least one polyamide polymer may be chosen from polyamide resins from vegetable sources. Polyamide resins from vegetable sources may be chosen from, for example, the polyamide resins of U.S. Pat. Nos. 5,783,657 and 5,998,570, the disclosures of which are herein incorporated by reference.

In one embodiment, the at least one polyamide polymer may be present in the composition in an amount ranging, for example, from 0.5% to 80%, such as from 2% to 60%, further such as from 5% to 40%, by weight relative to the total weight of the composition. In a further embodiment the at least one polyamide polymer may be present in the composition in an amount ranging, for example, from 5% to 25% by weight relative to the total weight of the composition.

In one embodiment, the at least one structuring polymer in the composition according to the invention corresponds to the polyamide polymers of formula (I). Due to fatty chain(s), these polymers may be readily soluble in oils and thus lead to compositions that are macroscopically homogeneous even with a high content (at least 25%) of at least one structuring polymer.

The at least one structuring polymer may have a softening point greater than 50° C., such as from 65° C. to 190° C., and further such as from 70° C. to 130° C., and even further such as from 80° C. to 105° C.

Film-Forming Silicone Resin

The at least one film-forming silicone resin of the compositions may be chosen from any silicone resin that has film forming properties. In one embodiment, the at least one film-forming silicone resin is chosen from silsesquioxanes and siloxysilicates.

The use of silicone polymers or derivatives as film-forming agents in cosmetic compositions is known in the art. See, e.g., U.S. Pat. Nos. 5,965,112; 5,800,816; 5,911,974; and 5,959,009, the disclosures of which are incorporated by reference herein. Silicone resin nomenclature is known in the art as "MDTQ" nomenclature, whereby a silicone resin is described according to the various monomeric siloxane repeating units which make up the polymer. Each letter of "MDTQ" denotes a different type of unit. The symbol M denotes the monofunctional unit $(CH_3)_3SiO_{1/2}$. The unit is considered monofunctional because the silicone atom only shares one oxygen for the formation of the chain.

The "M" unit can be represented as:

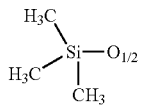

At least one of the methyl groups can be replaced, e.g., to give a unit with formula $[R(CH_3)_2]SiO_{1/2}$, as represented in the following structure:

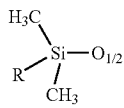

where R is other than a methyl group.

The symbol D denotes the difunctional unit $(CH_3)_2SiO2/2$ where two of the available bonds from the silicone atom are used for binding to oxygen for the formation of the polymeric chain. The "D" unit, which is the major building block of dimethicone oils, can be represented as:

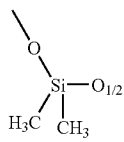

The symbol T denotes the trifunctional unit, $(CH_3)SiO_{3/2}$ and can be represented as

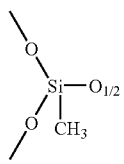

As in the M unit, any methyl group could be replaced in D or T with a group R which is other than methyl. Finally, the symbol Q denotes a quadrifunctional unit $SiO_{4/2}$ and can be represented as:

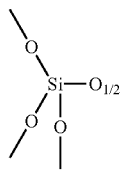

The number of different silicones which can be manufactured is staggering. It would be clear to one skilled in the art that the properties of each of the silicones will vary depending on the type of monomer, the type of substitution, the size of the polymeric chain, and the degree of cross linking or size of the side chain. Different properties are attained depending on whether the backbone is a silicone chain with carbon-based side chains or whether the backbone is carbon-based with silicone side chains.

As described above, the at least one film-forming silicone resin may be chosen from siloxysilicates and silsesquioxanes. Any siloxysilicates or silsesquioxanes that function as a film-former are within the practice of the invention. In one embodiment, the at least one film-forming silicone resin is chosen from substituted siloxysilicates and silsesquioxanes. A substituted siloxysilicate or a substituted silsesquioxane may be, for example, a siloxysilicate or a silsesquioxane where a methyl group has been substituted with a longer carbon chain such as an ethane, propane, or butane. The carbon chain may be saturated or unsaturated.

In one embodiment, the at least one film-forming silicone resin is chosen from siloxysilicates such as trimethylsiloxysilicates, which are represented by the following formula: $[(CH_3)_3-Si-O]_x-(SiO_{4/2})_y$ (MQ Units) where x and y can have values ranging from 50 to 80. In a further embodiment, a siloxysilicate may be chosen from any combination of M and Q units, such as, for example, $[(R)_3-Si-O]_x-(SiO_{4/2})_y$, where R is chosen from a methyl group and longer carbon chains.

In a further embodiment, the film-forming silicone resin is chosen from silsesquioxanes that are represented by the following formula: $(CH_3SiO_{3/2})_x$ (T Units) where x has a value of up to several thousand and the $CH_3$ may be replaced by an R, as described above for T units. In one embodiment, the silsesquioxane is chosen from polymethylsilsesquioxanes, which are silsesquioxanes that do not have a substituent replacing the methyl group. The polymethylsilsesquioxanes useful in the present invention are film-formers and can, for example, have about 500 or less T units, such as from about 50 to about 500 T units. In another embodiment, they have a melting point from about 40° C. to about 80° C. These silicone resins are soluble or dispersible in volatile silicones or other organic liquids.

Not all polymethylsilsesquioxanes are film-formers. For example, the highly polymerized polymethylsilsesquioxanes (T Resins), such as Tospearl™ from Toshiba or KMP590 from Shin-Etsu are highly insoluble and therefore are not effective film-formers. The molecular weight of these polymethylsilsesquioxanes is difficult to determine and they generally contain a thousand or more T units.

Other suitable polymethylsilsesquioxanes useful in accordance with the present invention include Belsil PMS MK, also referred to as Resin MK, available from Wacker Chemie. This polymethylsilsesquioxane is a polymer primarily formed of polymerized repeating units of $CH_3SiO_{3/2}$ (T units) and which can also contain up to about 1% (by weight or by mole) of $(CH_3)_2SiO2/2$ (D units). It is believed that the polymers are in a "cage" and "ladder" configuration as exemplified in the figure below. The weight-average molecular weight of the "cage" unit has been calculated to be 536. The majority of the polymer is in the "ladder" configuration, where the ends are capped with ethoxy $(CH_3CH_2O)$ groups. The weight percent of ethoxy present is about 4.5% and the mole percent is about 7% (silicone units). Since this functionality can react with water, a small and variable amount of SiOH can also be present. The weight-average molecular weight can be, for example, from about 500 to about 50,000, such as about 10,000.

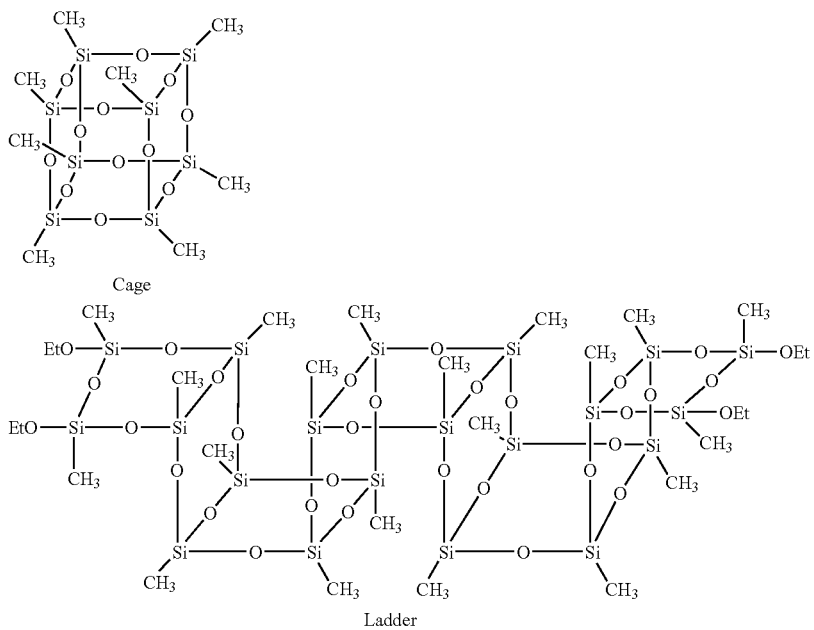
Cage

Ladder

Polymethylsilsesquioxanes suitable for use in the present invention also include KR-220L available from SHIN-ETSU. The structure of KR-220L is made up of mostly silicone T-units ($CH_3SiO_{3/2}$) with Si—OH or silanol end units. There are no D units. Other polymethylsilsesquioxanes that can be useful in the practice of the invention include KR-242A, which has a structure of about 98% methyl T units and about 2% dimethyl D units with Si—OH or silanol end units, and KR-251, which has a structure of about 88% methyl T units and about 12% dimethyl D units with Si—OH or silanol end units, both of which are available from SHIN-ETSU.

In a further embodiment, the at least one film-forming silicone resin is chosen from combinations of M, D, T, and Q units comprising at least two units chosen from M, D, T, and Q and that satisfy the relationship $R_nSiO_{(4-n)/2}$ wherein n is a value ranging from 1.0 to 1.50. Some resins of this type are disclosed in U.S. Pat. No. 6,074,654, the disclosure of which is incorporated by reference herein. R may be a methyl group or any carbon chain as long as the silicone resin retains its film forming properties. (Up to 5%, of silanol or alkoxy functionality may also be present in the resin structure as a result of processing.) The at least one film-forming silicone resins may be solid at about 25° C. and may have a molecular weight ranging from 1000 to 10000 grams/mole.

In a further embodiment, the at least one film-forming silicone resin comprises repeating M units and Q units. The ratio of M units to Q units may be, for example, 0.7:1. The at least one film-forming silicone resin may be chosen from Wacker 803 and 804 available from Wacker Silicones Corporation and G.E. 1170-002 from General Electric.

In a further embodiment, the at least one film-forming silicone resin is a copolymer wherein at least one unit of the copolymer is chosen from M, D, T, and Q silicone units and at least one additional unit of the copolymer is chosen from an ester. The at least one film-forming silicone resin may be chosen from, for example, diisostearoyl trimethylolpropane siloxysilicates, such as SF 1318, available from GE Silicones.

In one embodiment, the at least one film-forming silicone resin is present in the composition in an amount ranging from 0.5% to 20% by weight relative to the total weight of the composition, such as, for example 1% to 10%.

The compositions according to the present invention can additionally comprise at least one additional film-former. The at least one additional film-former may improve, for example, smoothness or spreadability, water-resistance, transfer resistance properties, or other cosmetic or pharmaceutical properties desired by one of skill in the art. The at least one additional film former may be chosen from, for example, polyethylene; vinylpyrrolidone/vinyl acetate (PVP/VA) copolymers such as the Luviskol® VA grades (all ranges) from BASF® Corporation and the PVP/VA series from ISP; acrylic fluorinated emulsion film formers including Foraperle® film formers such as Foraperle® 303 D from Elf Atochem (although Foraperle® may not be appropriate for some cosmetic formulations); GANEX® copolymers such as butylated PVP, PVP/Hexadecene copolymer, PVP/Eicosene copolymer or tricontanyl; Poly(vinylpyrrolidone/diethylaminoethyl methacrylate) or PVP/Dimethylaminoethylmethacrylate copolymers such as Copolymer 845; Resin ACO-5014 (Imidized IB/MA copolymer); other PVP based polymers and copolymers; alkyl cycloalkylacrylate copolymers (See WO 98/42298, the disclosure of which is hereby incorporated by reference); Mexomere® film formers and other allyl stearate/vinyl acetate copolymers (allyl stearate/VA copolymers); polyolprepolymers such as PPG-12/SMDI copolymer, polyolprepolymers such as PPG-1 2/SM DI copolymer, Poly(oxy-1,2-ethanediyl), α-hydro-ω-hydroxypolymer with 1,1'-methylene-bis-(4-isocyanatocyclohexane) available from Barnet; Avalure™ AC Polymers (Acrylates Copolymer) and Avalure™ UR polymers (Polyurethane Dispersions), available from BFGoodrich.

The at least one additional film former which also may be used within the framework of the invention includes film formers having any film former chemistry known in the art such as: PVP, acrylates, and urethanes; synthetic polymers of the polycondensate type or free-radical type, or ionic type, polymers of natural origin and mixtures thereof or any other film former known within the practice of the cosmetic and pharmaceutical arts which one skilled in the art may determine to be compatible.

An appropriate concentration of the at least one additional film former may be determined by one of skill in the art and can vary considerably based on the application. For example, for cosmetic compositions, at least one additional film former may be used in an amount from 0.1% to 20% such as, for example, from 1% to 10% by weight, relative to the total weight of the composition.

The concentrations of the at least one film-forming silicone resin and of the at least one structuring polymer may be chosen according to the desired hardness and desired stability of the compositions and according to the specific application envisaged. The respective concentrations of the at least one structuring polymer and of the at least one solid substance can be such that a disintegrable solid which does not flow under its own weight is obtained.

Depending on the intended application, such as a stick, hardness of the composition may also be considered. The hardness of a composition may, for example, be expressed in grams (g). The composition of the present invention may, for example, have a hardness ranging from 20 g to 2000 g, such as from 20 g to 900 g, and further such as from 20 g to 600 g.

This hardness is measured in one of two ways. A first test for hardness is according to a method of penetrating a probe into said composition and in particular using a texture analyzer (for example TA-XT2 from Rhéo) equipped with an ebonite cylinder of height 25 mm and diameter 8 mm. The hardness measurement is carried out at 20° C. at the center of 5 samples of said composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 g.

The second test for hardness is the "cheese wire" method, which involves cutting an 8.1 mm tube of composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 g to 300 g, such as from 30 g to 250 g, and further such as from 30 g to 200g.

The hardness of the composition of the present invention may be such that the compositions are self-supporting and can easily disintegrate to form a satisfactory deposit on a keratinous material. In addition, this hardness may impart good impact strength to the inventive compositions which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within the scope of the invention.

According to the present invention, the compositions in stick form may also possess the properties of deformable, flexible elastic solids and may also have noteworthy elastic softness upon application to a keratinous material. The compositions in stick form of the prior art do not have this elasticity and flexibility.

The at least one structuring polymer has an affinity with the fatty phase and in particular with a chemical portion of one of the oils forming the liquid fatty phase of the composition so that physical links with the oils, such as hydrogen bonds are formed.

Liquid Fatty Phase

The at least one liquid fatty phase, in one embodiment, may comprise at least one oil. The at least one oil, for example, may be chosen from polar oils and apolar oils including hydrocarbon-based liquid oils and oily liquids at room temperature. In one embodiment, the compositions of the invention comprise at least one structuring polymer and at least one polar oil. The polar oils of the invention, for example, may be added to the apolar oils, the apolar oils acting in particular as co-solvent for the polar oils.

According to the invention, the structuring of the at least one liquid fatty phase may, for example, be obtained with the aid of at least one polymer of formula (I). In general, the polymers of formula (I) may be in the form of mixtures of polymers, these mixtures also possibly containing a synthetic product corresponding to a compound of formula (I) in which n is 0, i.e., a diester.

The liquid fatty phase of the composition may contain more than 30%, for example, more than 40%, of liquid oil(s) containing a group similar to that of the units containing a hetero atom of the structuring polymer, and for example from 50% to 100%. In one embodiment, the liquid fatty phase structured with a polyamide-type skeleton contains a high quantity, i.e., greater than 30%, for example greater than 40% relative to the total weight of the liquid fatty phase, or from 50% to 100%, of at least one apolar, such as hydrocarbon-based, oil. For the purposes of the invention, the expression "hydrocarbon-based oil" means an oil essentially comprising carbon and hydrogen atoms, optionally with at least one group chosen from hydroxyl, ester, carboxyl, and ether groups.

For a liquid fatty phase structured with a polymer containing a partially silicone-based skeleton, this fatty phase may contain more than 30%, for example, more than 40%, relative to the total weight of the liquid fatty phase and, for example, from 50% to 100%, of at least one silicone-based liquid oil, relative to the total weight of the liquid fatty phase.

For a liquid fatty phase structured with an apolar polymer of the hydrocarbon-based type, this fatty phase may contain more than 30%, for example more than 40% by weight, or from 50% to 100% by weight, of at least one liquid apolar, such as hydrocarbon-based, oil, relative to the total weight of the liquid fatty phase.

For example, the at least one polar oil useful in the invention may be chosen from:

hydrocarbon-based plant oils with a high content of triglycerides comprising fatty acid esters of glycerol in which the fatty acids may have varied chain lengths from $C_4$ to $C_{24}$, these chains possibly being chosen from linear and branched, and saturated and unsaturated chains; these oils are chosen from, for example, wheat germ oil, corn oil, sunflower oil, karite butter, castor oil, sweet almond oil, macadamia oil, apricot oil, soybean oil, cotton oil, alfalfa oil, poppy oil, pumpkin oil, sesame oil, marrow oil, rapeseed oil, avocado oil, hazelnut oil, grape seed oil, blackcurrant seed oil, evening primrose oil, millet oil, barley oil, quinoa oil, olive oil, rye oil, safflower oil, candlenut oil, passion flower oil and musk rose oil; or alternatively caprylic/capric acid triglycerides such as those sold by Stearineries Dubois or those sold under the names Miglyol 810, 812 and 818 by Dynamit Nobel;

synthetic oils or esters of formula $R_5COOR_6$ in which $R_5$ is chosen from linear and branched fatty acid residues containing from 1 to 40 carbon atoms and $R_6$ is chosen from, for example, a hydrocarbon-based chain containing from 1 to 40 carbon atoms, on condition that $R_5+R_6 \geq 10$, such as, for example, purcellin oil (cetostearyl octanoate), isononyl isononanoate, $C_{12}$-$C_{15}$ alkyl benzoates, isopropyl myristate, 2-ethylhexyl palmitate, isostearyl isostearate and alkyl or polyalkyl octanoates, decanoates or ricinoleates; hydroxylated esters such as isostearyl lactate and diisostearyl malate; and pentaerythritol esters;

synthetic ethers containing from 10 to 40 carbon atoms;

$C_8$ to $C_{26}$ fatty alcohols such as oleyl alcohol; and $C_8$ to $C_{26}$ fatty acids such as oleic acid, linolenic acid or linoleic acid.

The at least one apolar oil according to the invention is chosen from, for example, silicone oils chosen from volatile and non-volatile, linear and cyclic polydimethylsiloxanes (PDMSs) that are liquid at room temperature; polydimethylsiloxanes comprising alkyl or alkoxy groups which are pendant and/or at the end of the silicone chain, the groups each containing from 2 to 24 carbon atoms; phenylsilicones such as phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates; hydrocarbons chosen from linear and branched, volatile and non-volatile hydrocarbons of synthetic and mineral origin, such as volatile liquid paraffins (such as isoparaffins and isododecane) or non-volatile liquid paraffins and derivatives thereof, liquid petrolatum, liquid lanolin, polydecenes, hydrogenated polyisobutene such as Parleam®, and squalane; and mixtures thereof. The structured oils, for example those structured with polyamides such as those of formula (I) or the polyurethanes or polyureas or polyureaurethanes, may be, in one embodiment, apolar oils, such as an oil or a mixture of hydrocarbon oils chosen from those of mineral and synthetic origin, chosen from hydrocarbons such as alkanes such as Parleam® oil, isoparaffins including isododecane, and squalane, and mixtures thereof. These oils may, in one embodiment, be combined with at least one phenylsilicone oil.

The liquid fatty phase, in one embodiment, contains at least one non-volatile oil chosen from, for example, hydrocarbon-based oils of mineral, plant and synthetic origin, synthetic esters or ethers, silicone oils and mixtures thereof.

In practice, the total liquid fatty phase may be present, for example, in an amount ranging from 1% to 99% by weight relative to the total weight of the composition; further examples include ranges of 5 to 95.5%, 10% to 80% and 20% to 75%.

For the purposes of the invention, the expression "volatile solvent or oil" means any non-aqueous medium capable of evaporating on contact with the skin or the lips in less than one hour at room temperature and atmospheric pressure. The volatile solvent(s) of the invention is(are) organic solvents, such as volatile cosmetic oils that are liquid at room temperature, having a non-zero vapor pressure, at room temperature and atmospheric pressure, ranging in particular from $10^{-2}$ to 300 mmHg and, for example, greater than 0.3 mmHg. The expression "non-volatile oil" means an oil which remains on the skin or the lips at room temperature and atmospheric pressure for at least several hours, such as those having a vapor pressure of less than $10^{-2}$ mmHg.

According to the invention, these volatile solvents may facilitate the staying power or long wearing properties of the composition on the skin, the lips or superficial body growths. The solvents can be chosen from hydrocarbon-based solvents, silicone solvents optionally comprising alkyl or alkoxy groups that are pendant or at the end of a silicone chain, and a mixture of these solvents.

The volatile oil(s), in one embodiment, is present in an amount ranging from 0% to 95.5% relative to the total weight of the composition, such as from 2% to 75% or, for example, from 10% to 45%. This amount will be adapted by a person skilled in the art according to the desired staying power or long wearing properties.

The at least one liquid fatty phase of the compositions of the invention may further comprises a dispersion of lipid vesicles. The compositions of the invention may also, for example, be in the form of a fluid anhydrous gel, a rigid anhydrous gel, a fluid simple emulsion, a fluid multiple emulsion, a rigid simple emulsion or a rigid multiple emulsion. The simple emulsion or multiple emulsion may comprise a continuous phase chosen from an aqueous phase optionally containing dispersed lipid vesicles or oil droplets, or a fatty phase optionally containing dispersed lipid vesicles or water droplets. In one embodiment, the composition has a continuous oily phase or fatty phase and is more specifically an anhydrous composition, for example, a stick or dish form. An anhydrous composition is one that has less than 10% water by weight, such as, for example, less than 5% by weight.

The compositions of the invention may further comprise at least one additional fatty material. The at least one additional fatty material may, for example, be chosen from gums, fatty materials pasty at ambient temperature, and resins.

The composition of the present invention may also further comprise at least one suitable additive commonly used in the field concerned chosen from coloring agents, antioxidants, essential oils, preserving agents, fragrances, fillers, pasty fatty substances, waxy fatty substances, neutralizing agents, liposoluble polymers, and cosmetically active agents and dermatological active agents such as, for example, emollients, moisturizers, vitamins, essential fatty acids and sunscreens. The compositions of the invention may also further comprise water optionally thickened with an aqueous-phase thickener or gelled with a gelling agent and/or containing ingredients soluble in water.

In one embodiment, the at least one suitable additive is chosen from a wax. As used herein, a "wax" may be any lipophilic fatty compound. Non-limiting examples of such waxes include waxes of natural origin, such as beeswax, carnauba wax, candelilla wax, ouricury wax, Japan wax, cork fiber wax, sugar cane wax, paraffin waxes, lignite wax, microcrystalline waxes, lanolin wax, montan wax and ozokerites, hydrogenated oils such as hydrogenated jojoba oil, jojoba esters, waxes of synthetic origin, such as polyethylene waxes derived from polymerization of ethylene, waxes obtained by Fischer-Tropsch synthesis, fatty acid esters and glycerides, and silicone waxes such as derivatives of poly(di)methylsiloxane. The wax, in one embodiment, is present in an amount ranging from 0.5% to 15% relative to the total weight of the composition, such as from 0.1% to 10%.

Another embodiment of the invention relates to a skin lip, or keratinous fiber care or make-up composition comprising a structured composition containing at least one liquid fatty phase structured with at least one structuring polymer comprising a polymer skeleton comprising at least one hydrocarbon-based repeating unit comprising at least one hetero atom and at least one film-forming silicone resin.

Additionally, an embodiment of the invention relates to a skin, lip, or keratinous fiber care or make-up composition comprising a structured composition containing at least one liquid fatty phase structured with at least one structuring polymer comprising a polymer skeleton comprising at least one hydrocarbon-based repeating unit comprising at least one hetero atom, at least one film-forming silicone resin, and at least one coloring agent.

Additionally, an embodiment of the invention relates to a method of making up skin, lips, or keratinous fibers or caring for skin, lips, or keratinous fibers comprising applying to said skin, lips, or keratinous fibers a structured composition containing at least one liquid fatty phase structured with at least one structuring polymer comprising a polymer skeleton comprising at least one hydrocarbon-based repeating unit comprising at least one hetero atom and at least one film-forming silicone resin.

Needless to say, the person skilled in the art will take care to select the optional additional additives and the amount thereof such that not all of the possible advantageous properties of the composition according to the invention are, or are substantially, adversely affected by the addition(s) envisaged.

The transfer resistance of a composition may be evaluated by a transfer resistance test. A composition is applied to the clean, bare skin of a group of subjects as a smooth, thin layer, such as a 1"×1" square in size. The composition is allowed to air dry for 5 minutes and using a facial tissue or other cloth or sponge and medium pressure the area is wiped as if attempting to wipe the product off of the skin. The subjects are then asked to evaluate the results. Positive results are described as the presence of a makeup film that could not be easily removed without soap and water. For example, the results may be rated on a scale of 1 to 5 with 5 being the best and 1 being the worst.

The packaging and application device for any subject of the invention may be chosen and manufactured by persons skilled in the art on the basis of their general knowledge, and adapted according to the nature of the composition to be packaged. Indeed, the type of device to be used can be in particular linked to the consistency of the composition, in particular to its viscosity; it can also depend on the nature of the constituents present in the composition, such as the presence of volatile compounds.

The present invention is also directed to a cosmetic process for caring for, making up or treating a keratinous material, such as that of a human being, and further such as human skin, lips, or keratinous fibers, comprising the application to a keratinous material of a cosmetic composition comprising at least one polyamide polymer comprising a polyamide skeleton. The polyamide skeleton comprises at least one end group with at least one chain chosen from alkyl chains comprising at least four carbon atoms and alkenyl chains comprising at least four carbon atoms, bonded to the at least one polyamide skeleton via at least one linking group. The polyamide skeleton may further comprise at least one pendant group with at least one chain chosen from alkyl chains comprising at least four carbon atoms and alkenyl chains comprising at least four carbon atoms, bonded to any carbon or nitrogen of the polyamide skeleton via at least one linking group. The composition also comprises at least one film-forming silicone resin.

In another embodiment, the present invention is directed to a process of making a cosmetic composition in the form of a physiologically acceptable composition comprising including in said composition at least one polyamide polymer comprising a polyamide skeleton. The polyamide skeleton comprises at least one end group with at least one chain chosen from alkyl chains comprising at least four carbon atoms and alkenyl chains comprising at least four carbon atoms, bonded to the at least one polyamide skeleton via at least one linking group. The polyamide skeleton may further comprise at least one pendant group with at least one chain chosen from alkyl chains comprising at least four carbon atoms and alkenyl chains comprising at least four carbon atoms, bonded to any carbon or nitrogen of the polyamide skeleton via at least one linking group. The composition also comprises at least one film-forming silicone resin.

Another embodiment of the invention relates to a lipstick composition in stick form comprising at least one continuous liquid fatty phase, at least one film-forming silicone resin and at least one non-waxy structuring polymer having a weight-average molecular mass of less than 100 000, the continuous liquid fatty phase, the at least one film-forming silicone resin for the fatty phase and the at least one non-waxy structuring polymer being present in the composition.

The invention will be illustrated by, but is not intended to be limited to, the following examples.

EXAMPLE 1

Transfer Resistant Mascara

A transfer resistant mascara was prepared by mixing the following ingredients.

| PHASE | INCI NAME | w/w % |
| --- | --- | --- |
| A | Isododecane | 41.97 |
|   | Alkyl Silicone Resin with Alkyl Groups (MK Resin) | 7.00 |
|   | Isododecane Gel (Versagel MD 870) | 16.50 |
|   | Quaternium 18 Hectorite | 4.00 |
|   | Black Iron Oxide | 5.00 |
| B | Propylene Carbonate | 1.32 |
| C | Paraffin | 3.00 |
|   | Carnauba Wax | 5.20 |
|   | Beeswax | 7.00 |
|   | Synthetic Beeswax | 4.00 |
|   | Uniclear 100 | 5.00 |
|   | Phenoxyethanol | 0.01 |

Phases A, B, and C were each prepared separately by mixing together the ingredients of each phase. The three phases were then combined and the resulting mascara was found to have transfer resistant properties upon application to eye lashes.

EXAMPLE 2

Transfer Resistant Mascara

A transfer resistant mascara was prepared from the following ingredients.

| PHASE | INCI NAME | w/w % |
| --- | --- | --- |
| A | Isododecane | 40.4 |
|   | Trimethylsiloxysilicate | 7.0 |
|   | Isododecane with a) styrene-ethylene/butylene-styrene | 14.0 |
|   | triblock copolymer, and | 1.24 |
|   | b) styrene-ethylene/propylene radial copolymer | 1.24 |
|   | Disteardimonium Hectorite | 5.5 |
|   | Iron Oxides | 5.0 |
| B | Propylene Carbonate | 1.8 |
| C | Allyl stearate/VA copolymer | 5.0 |
|   | Waxes | 6.8 |
|   | Preservatives | 0.01 |
|   | Uniclear 100 | 2.00 |

Phase A was mixed with a homogenizer for 20 minutes at room temperature and then heated to 65° C. for 15 minutes. In a separate beaker, phase C was combined with propeller mixing and heated to 85-90° C. Once phase A and phase C reached their respective temperatures, phase C was added to phase A. The batch was homogenized for 5 minutes while maintaining the heat at 80-85° C. and phase B was added. The mixture was homogenized for 30 minutes at 80-85° C. and then removed from the homogenizer and cooled to 30-35° C. using sweep mixing. The ingredients were combined and the resulting mascara was found to have transfer resistant properties upon application to eye lashes.

The present invention may be embodied in other specific forms without departing from its spirit or essential characteristics. The described embodiments are to be considered in all respects as illustrative only and not restrictive. The scope of the invention is, therefore, indicated by the appended claims, rather than by the foregoing description. All changes which come within the meaning and range of equivalency of the claims are to be embraced within their scope.

What is claimed is:

1. A cosmetic composition comprising:
   at least one liquid fatty phase in said cosmetic composition which comprises:
   (i) at least one structuring polymer chosen from ethylenediamine/stearyl dimer dilinoleate copolymer and ethylenediamine/stearyl dimer tallate copolymer; and
   (ii) at least one film-forming silicone resin.

2. A cosmetic composition comprising:
   at least one liquid fatty phase which comprises:
   (i) at least one structuring polymer chosen from ethylenediamine/stearyl dimer dilinoleate copolymer and ethylenediamine/stearyl dimer tallate copolymer; and
   (ii) at least one film-forming silicone resin.

3. A method comprising applying a cosmetic composition to a keratin material, said cosmetic composition comprising:
   at least one liquid fatty phase which comprises:
   (i) at least one structuring polymer chosen from ethylenediamine/stearyl dimer dilinoleate copolymer and ethylenediamine/stearyl dimer tallate copolymer; and
   (ii) at least one film-forming silicone resin.

4. A method for making a cosmetic composition in the form of a physiologically acceptable composition comprising including in said composition
   at least one liquid fatty phase which comprises:
   (i) at least one structuring polymer chosen from ethylenediamine/stearyl dimer dilinoleate copolymer and ethylenediamine/stearyl dimer tallate copolymer; and
   (ii) at least one film-forming silicone resin.

* * * * *